(12) United States Patent
Gu et al.

(10) Patent No.: US 10,502,732 B2
(45) Date of Patent: Dec. 10, 2019

(54) DETECTION OF PATHOGENS USING UNMODIFIED METAL NANOPARTICLES

(71) Applicants: Frank X. Gu, Kitchener (CA); Lyndon W. Jones, Waterloo (CA); Mohit S. Verma, Brampton (CA); Paul Chen, Calgary (CA)

(72) Inventors: Frank X. Gu, Kitchener (CA); Lyndon W. Jones, Waterloo (CA); Mohit S. Verma, Brampton (CA); Paul Chen, Calgary (CA)

( * ) Notice: Subject to any disclaimer, the term of this patent is extended or adjusted under 35 U.S.C. 154(b) by 0 days.

(21) Appl. No.: 14/893,297

(22) PCT Filed: May 23, 2014

(86) PCT No.: PCT/CA2014/050482
§ 371 (c)(1),
(2) Date: Nov. 23, 2015

(87) PCT Pub. No.: WO2014/186901
PCT Pub. Date: Nov. 27, 2014

(65) Prior Publication Data
US 2016/0123967 A1 May 5, 2016

Related U.S. Application Data

(60) Provisional application No. 61/855,811, filed on May 24, 2013.

(51) Int. Cl.
*G01N 33/543* (2006.01)
*C12Q 1/04* (2006.01)
(Continued)

(52) U.S. Cl.
CPC ......... *G01N 33/54346* (2013.01); *C12Q 1/04* (2013.01); *G01N 33/56911* (2013.01); *B82Y 30/00* (2013.01); *G01N 31/22* (2013.01)

(58) Field of Classification Search
CPC ... C12Q 1/70; C12Q 1/68; C12Q 1/04; G01N 31/22; G01N 33/54346; G01N 33/56911; B82Y 30/00
(Continued)

(56) References Cited

U.S. PATENT DOCUMENTS

2005/0059042 A1 3/2005 Rothberg et al.
2008/0268450 A1 10/2008 Nam et al.
2012/0302940 A1 11/2012 Ray

FOREIGN PATENT DOCUMENTS

WO WO 2012/139122 * 10/2012 ............... C12Q 1/68
WO WO-2012/139122 A1 10/2012

OTHER PUBLICATIONS

Hussain et al. Clin.Biochem. Jan. 11, 2013. vol. 46, issue 7-8, pp. 633-637.*
(Continued)

*Primary Examiner* — Jana A Hines
(74) *Attorney, Agent, or Firm* — Foley Hoag LLP

(57) ABSTRACT

The present disclosure relates to a method for the direct detection of pathogen in a sample using unmodified metallic nanoparticles, such as gold nanoparticles. The method may employ colorimetric detection. The combination of unmodified metallic nanoparticles and colorimetric detection provides a method that is simple, rapid, and economical compared to prior art methods that require modified nanoparticles or expensive detection equipment. The method does not require labeling of the target pathogen and is capable of detecting a broad spectrum of pathogens.

16 Claims, 12 Drawing Sheets

• Star Center
◯ Star Core
┝━━┥ Total diameter
┝┄┄┄┤ Minor diameter
┝┄┄┄┤ Branch length
┝━━┥ Branch width

(51) Int. Cl.
G01N 33/569 (2006.01)
G01N 31/22 (2006.01)
B82Y 30/00 (2011.01)

(58) Field of Classification Search
USPC .................................. 435/5, 7.32; 436/6.11
See application file for complete search history.

(56) References Cited

OTHER PUBLICATIONS

Hussain et al. (Unmodified gold nanoparticles for direct and rapid detection of *Mycobacterium tuberculosis* complex. Clinical Biochemistry, 46, pp. 633-637, Jan. 11, 2013 (Nov. 1, 2013)).*
Kanjanawarut et al., (Anal. Chem., 2009, 81 (15), pp. 6122-6129).*
Wang et al., (vol. 4, Issue 12. Dec. 2008 pp. 2204-2208).*
Gevorkian et al., (Biochem J. Apr. 15, 2005; 387(Pt 2):411-417).*
Navarre et al., (Microbiol. Mol. Biol Rev. Mar. 1999; 63(1): 174-229).*
Wang et al., (vol. 4, Issue 12. Dec. 2008 pp. 2204-2208). (Year: 2008).*
Wu et al., (J. Mass. Spectrom. 2012, 47, 355-363). (Year: 2012).*
Lee et al., (Biosensors and Bioelectronics. vol. 31 (Issue 1), Jan. 2012, pp. 77-83). (Year: 2012).*
Berry et al., "Deposition of CTAB-Terminated Nanorods on Bacteria to Form Highly Conducting Hybrid Systems", Journal of the American Chemical Society, Dec. 2005, vol. 127 (50), pp. 17600-17601.
Berry et al., "Self-Assembly of Nanoparticles on Live Bacterium: an Avenue to Fabricate Electronic Devices", Angewandte Chemie, Oct. 2005, vol. 44 (41), pp. 6668-6673.
Chen et al., "Controlling the Length and Shape of Gold Nanorods", The Journal of Physical Chemistry. B, Oct. 2005, vol. 109 (42), pp. 19553-19555.
Dantam et al., "Biocidal Efficacy of Silver-Impregnated Contact Lens Storage Cases in Vitro", Investigative Ophthalmology and Visual Science, Jan. 2011, vol. 52 (1), pp. 51-57.
Grzelczak et al., "Shape Control in Gold Nanoparticle Synthesis", Chemical Society Reviews, Jul. 2008, vol. 37 (9), pp. 1783-1791.
Hao et al., "Plasmon Resonances of a Gold Nanostar", Nano Letters, Feb. 2007, vol. 7 (3), pp. 729-732.
Hayden et al., "Aggregation and Interaction of Cationic Nanoparticles on Bacterial Surfaces", Journal of the American Chemical Society, Apr. 2012, vol. 134 (16), pp. 6920-6923.
Ho et al., "Using Biofunctionalized Nanoparticles to Probe Pathogenic Bacteria", Analytical Chemistry, Dec. 2004, vol. 76 (24), pp. 7162-7166.
Hong et al., "Cell Surface Acid-Base Properties of *Escherichia coli* and *Bacillus brevis* and Variation as a Function of Growth Phase, Nitrogen Source and C:N Ratio", Colloids and surfaces. B, Biointerfaces Jul. 2006, vol. 50 (2), pp. 112-119.
Hong et al., "Electrostatic Behavior of the Charge-Regulated Bacterial Cell Surface", Langmuir: The ACS Journal of Surfaces and Colloids, May 2008, vol. 24 (9), pp. 5003-5009.
Hussain et al., "Unmodified Gold Nanoparticles for Direct and Rapid Detection of *Mycobacterium tuberculosis* Complex", Clinical Biochemistry, Jan. 2013, vol. 46 (7-8), pp. 633-637.
International Patent Application No. PCT/CA2014/050482, International Preliminary Report on Patentability dated Dec. 3, 2015.
International Patent Application No. PCT/CA2014/050482, International Search Report and Written Opinion dated Aug. 7, 2014.
Khan et al., "Targeted Highly Sensitive Detection of Multi-Drug Resistant *Salmonella* DT104 Using Gold Nanoparticles", Chemical communications (Cambridge, England), Sep. 2011, vol. 47 (33), pp. 9444-9446.

Kilvington et al., "Identification and Susceptibility to Multipurpose Disinfectant Solutions of Bacteria Isolated from Contact Lens Storage Cases of Patients with Corneal Infiltrative Events", Contact Lens and Anterior Eye, Dec. 2013, vol. 36 (6), pp. 294-298.
Link et al., "Shape and Size Dependence of Radiative, Non-Radiative and Photothermal Properties of Gold Nanocrystals", International Reviews in Physical Chemistry, Jul. 2000, vol. 19 (3), pp. 409-453.
Lu et al., "Gold Nano-Popcorn-Based Targeted Diagnosis, Nanotherapy Treatment, and in Situ Monitoring of Photothermal Therapy Response of Prostate Cancer Cells Using Surface-Enhanced Raman Spectroscopy", Journal of the American Chemical Society, Dec. 2010, vol. 132 (51), pp. 18103-18114.
Min-Chen et al., "A Versatile Route to the Controlled Synthesis of Gold Nanostructures", Crystal Growth and Design, Mar. 2009, vol. 9 (5), pp. 2079-2087.
Nehl et al., "Optical Properties of Star-Shaped Gold Nanoparticles," Nano Letters, Mar. 2006, vol. 6 (4), pp. 683-688.
Phillips et al., "Rapid and Efficient Identification of Bacteria Using Gold-Nanoparlicle-Poly (Para-Phenyleneethynylene) Constructs", Angewandte Chemie, Mar. 2008, vol. 47 (14), pp. 2590-2594.
Sau et al., "Nonspherical Noble Metal Nanoparticles: Colloid-Chemical Synthesis and Morphology Control," Advanced Materials, Apr. 2010, vol. 22 (16), pp. 1781-1804.
Scott et al., "Surface Proteins of Gram-Positive Bacteria and how they Get there", Annual Review of Microbiology, Oct. 2006, vol. 60, pp. 397-423.
Sha et al., "Utilization of Unmodified Gold Nanoparticles in Colorimetric Detection," Science China-Physics, Mechanics & Astronomy, Oct. 2011, vol. 54 (10), pp. 1757-1765.
Shawky et al., "Direct Detection of Unamplified Hepatitis C Virus RNA Using Unmodified Gold Nanoparticles", Clinical Biochemistry, Aug. 2010, vol. 43 (13-14), pp. 1163-1168.
Sun et al., "A Facile Assay for Direct Colorimetric Visualization of Lipopolysaccharides at Low Nanomolar Level", Nano Research, Jul. 2012, vol. 5 (7), pp. 486-493.
Sun et al., "Shape-Controlled Synthesis of Gold and Silver Nanoparticles", Science, Dec. 2002, vol. 298 (5601), pp. 2176-2179.
Verma et al., "Branching and Size of Ctab-Coated Gold Nanostars Control the Colorimetric Detection of Bacteria", RSC Advances, Feb. 2014, vol. 4 (21), pp. 10660-10668.
Wang et al., "Gold Nanorod Probes for the Detection of Multiple Pathogens", Small, Nov. 2008, vol. 4 (12), pp. 2204-2208.
Wu et al., "Future Perspective of Nanoparticle Interaction-assisted Laser Desorption/Ionization Mass Spectrometry for Rapid, Simple, Direct and Sensitive Detection of Microorganisms", Journal of Mass Spectrometry, Mar. 2012, vol. 47 (3), pp. 355-363.
Wu et al., "Seed-Mediated Synthesis of Branched Gold Nanocrystals Derived from the Side Growth of Pentagonal Bipyramids and the Formation of Gold Nanostars", Chemistry of Materials, 2009, vol. 21 (1), pp. 110-114.
Xia et al., "Colorimetric Detection of DNA, Small Molecules, Proteins, and Ions Using Unmodified Gold Nanoparticles and Conjugated Polyelectrolytes", Proceedings of the National Academy of Sciences of the United States of America, Jun. 2010, vol. 107 (24), pp. 10837-10841.
Xiao et al., "Surfactant-Assisted, Shape-Controlled Synthesis of Gold Nanocrystals", Nanoscale, Feb. 2011, vol. 3 (4), pp. 1383-1396.
Yuan et al., "Gold Nanostars: Surfactant-Free Synthesis, 3D Modelling, and Two-Photon Photoluminescence Imaging", Nanotechnology, Feb. 2012, vol. 23 (7), pp. 075102.

* cited by examiner

DETECTION OF PATHOGENS USING UNMODIFIED METAL NANOPARTICLES

CROSS REFERENCE TO RELATED APPLICATIONS

This application is the U.S. national phase of International Patent Application No. PCT/CA2014/050482, filed May 23, 2014, which claims the benefit of priority of U.S. Provisional Patent Application No. 61/855,811, filed May 24, 2013, which is hereby incorporated by reference.

FIELD

The present disclosure relates to a method for the detection of pathogens using unmodified metallic nanoparticles.

BACKGROUND

Metallic nanoparticles have been the subject of extensive research due to their unique optical, electronic, and molecular-recognition properties. They have applications in a wide variety of areas, including chemical analysis, medical diagnosis and environmental monitoring. Metallic nanoparticles are emerging as promising biosensors because of their unique properties and ability to interact with biomolecules. For example, metallic nanoparticles have been explored for the detection of oligonucleotides, proteins and cells.

US 2005/0059042 A1 describes a method of oligonucleotide detection utilizing gold nanoparticles with either single stranded (ss) or double stranded (ds) deoxyribonucleic acid (DNA). Electrostatic interactions were used to distinguish between ssDNA and dsDNA because ssDNA adsorbs on gold and prevents their aggregation in a salt solution while dsDNA does not prevent aggregation. This aggregation leads to color change and thus, ssDNA remains pink while dsDNA turns blue. This method is limited to oligonucleotides and requires the use of salt for aggregation of nanoparticles.

US 2008/0268450 A1 describes a method of detecting proteins using surface modified magnetic nanoparticles along with gold nanoparticles. The magnetic nanoparticles are modified with antibodies against the protein of interest as well as specific oligonucleotide sequences. The gold nanoparticles are modified with complimentary oligonucleotide sequence. The protein of interest is first concentrated by separation using the magnetic nanoparticles. These particles are then complexed with the gold nanoparticles and detection is performed using thin layer chromatography (TLC) chips. This approach requires the use of a magnet for protein separation and also additional TLC chips for separation of gold nanoparticles. Thus, several steps are involved in detection.

WO 2012/139122 A1 describes a gold nanoparticle-based colorimetric assay for detecting nucleic acids from viral, bacterial and other microorganisms in clinical specimens using unmodified gold nanoparticles and specific oligotargeter polynucleotides that bind to the pathogen-specific nucleic acids.

US 2012/0302940 A1 describes functionalized gold nanoparticles for use in the treatment of cancer cells and pathogenic bacteria. In this case, the nanoparticles were modified with specific oligonucleotides or antibodies that would bind to cancer cells or bacteria. The cells were characterized using Raman spectroscopy before and after photothermal treatment. The absence of a Raman spectrum after treatment demonstrated the effectiveness of the treatment at killing the respective cells. This technique requires the use of a specific label for the cells and also a Raman spectrometer for quantification of the cells.

Methods employing modified metallic nanoparticles can suffer from several disadvantages. For example, different functionalized nanoparticles are required for different targets; separation of ligands for functionalizing nanoparticles (such as DNA) can be costly; covalent conjugation of bioactive ligands onto the surface of nanoparticles could reduce their reactivity. Furthermore, methods employing modified nanoparticles can be time-consuming, require numerous reagents and steps, and require expensive equipment and/or specialized expertise.

It is desirable to provide detection methods using metallic nanoparticles that do not require modification. In particular, it is desirable to provide a simple method for the detection of pathogens using unmodified metallic nanoparticles.

SUMMARY

The present disclosure relates to a method for the detection of pathogens using unmodified metal nanoparticles, such as gold nanoparticles.

In one aspect, there is provided a method of detecting a pathogen in a sample comprising: contacting a sample with a plurality of unmodified metallic nanoparticles under conditions suitable to permit association of the nanoparticles with the pathogen, if present; and assessing the association of the nanoparticles with the pathogen (e.g. the surface of the pathogen) to determine whether the pathogen is present or absent. In some embodiments, the method is a colorimetric method.

In one aspect, there is provided a colorimetric method for detecting a pathogen in a sample comprising: contacting a sample with a plurality of unmodified metallic nanoparticles under conditions suitable to permit association of the nanoparticles with the pathogen, if present; assessing a colorimetric property of the sample to determine whether the pathogen is present or absent.

In some embodiments, assessing comprises comparing the colorimetric property of the sample to a control. In some embodiments, the colorimetric property is assessed visually. In some embodiments, the colorimetric property is assessed using a spectrophotometer, such as a UV-Visible spectrophotometer.

In some embodiments, the metallic nanoparticles are gold nanoparticles.

In some embodiments, the nanoparticles are less than about 1000 nm, less than about 500 nm, less than about 400 nm, less than about 300 nm, less than about 200 nm, less than about 150 nm, less than 100 nm, less than 90 nm, less than about 80 nm, less than about 70 nm, less than about 60 nm, less than about 50 nm, less than about 40 nm, less than about 35 nm, less than about 30 nm, less than about 25 nm, less than about 20 nm, less than about 15 nm, less than about 10 nm, less than about 9 nm, less than about 8 nm, less than about 7 nm, less than about 6 nm, less than about 5 nm, less than about 4 nm, less than about 3 nm, less than about 2 nm, less than about 1 nm.

In some embodiments, the nanoparticles are between about 1 nm and about 1000 nm, between about 10 nm and about 1000 nm, between about 1 nm and about 500 nm, between about 10 nm and about 500 nm, between about 1 nm and about 250 nm, between about 10 nm and about 250 nm, between about 1 nm and about 200 nm, between about 10 nm and about 200 nm, between about 1 nm and about 150 nm, between about 10 nm and about 150 nm, between about 1 nm and about 100 nm, between about 10 nm and about 100 nm, between about 1 nm and about 80 nm, between about 10 nm and about 80 nm, between about 1 nm and about 60 nm, between about 10 nm and about 60 nm, between about 1 nm and about 50 nm, between about 10 nm and about 50 nm, between about 1 nm and about 40 nm, between about 10 nm and about 40 nm, between about 1 nm and about 30 nm, between about 10 nm and about 30 nm, between about 1 nm and about 20 nm, between about 10 nm and about 20 nm, between about 1 nm and about 10 nm, between about 1 nm and about 5 nm, between about 1 nm and about 4 nm, between about 1 nm and about 3 nm, or between about 1 nm and about 2 nm. In some embodiments, the nanoparticles are in the range of about 10 to about 200 nm.

In some embodiments, the nanoparticles have branches. In some embodiments, the nanoparticles have 1 to 20 branches, 1 to 15 branches, 1 to 10 branches, 1 to 9 branches, 1 to 8 branches, 1 to 7 branches, 1 to 6 branches, 1 to 5 branches, 1 to 4 branches, 1 to 3 branches, 1 to 2 branches. In some embodiments, the nanoparticles have 1, 2, 3, 4, 5, 6, 7, 8, 9, 10, 11, 12, 13, 14, 15, 16, 17, 18, 19 or 20 branches. In some embodiments, the nanoparticles have 1 to 15 branches.

In some embodiments, the nanoparticles comprise a mixture of two or more distinct populations of nanoparticles.

In some embodiments, the pathogen is selected from bacteria, virus, fungi, protozoa and prion. In some embodiments, the pathogen is bacteria. In some embodiments, the bacteria is selected from the group consisting of *Staphylococcus aureus, Streptococcus pneumoniae, Enterococcus faecalis, Achromobacter xylosoxidans, Escherichia coli, Delftia acidovorans, Pseudomonas aeruginosa, Serratia marcescens, Stenotrophomonas maltophilia, Amycolatopsis azurea, Amycolatopsis orientalis, Bacillus lichenformis, Bacillus subtilis, Lactococcus lactis, Lactobacillus plantarum, Pseudomonas putida, Streptomyces coelicolor, Streptomyces griseus, Shewanella oneidensis, Vibrio fischeri, Vibrio alginolyticus, Micrococcus luteus, Pichia pastoris, Edwardsiella tarda, Elizabethkingia meningoseptica, Salmonella typhi, Salmonella typhimurium, Salmonella enterica, Staphylococcus epidermis, Kelbsiella pneumoniae, Bacillus cereus, Mycobacterium tuberculosis, Acinetobacter baumannii, Helicobacter pylori, Listeria monocytogenes, Bacillus anthracis, Chlamydia trachomatis, Neisseria gonorrhoeae, Treponema pallidum, Campylobacter jejuni, Legionella pneumophila, Haemophilus influenza,* or *Clostridium difficile.*

In some embodiments, the conditions suitable to permit association of the nanoparticles with the pathogen, if present, comprise a contact period at least 5 seconds, at least 10 seconds, at least 30 seconds, at least 1 minute, at least 5 minutes, at least 10 minutes, at least 30 minutes, at least 1 hour, at least 5 hours, at least 8 hours, at least 12 hours, about 5 seconds to about 12 hours, about 10 seconds to about 1 hour, about 10 seconds to about 10 minutes, about 1 minute to about 1 hour, about 1 hour to about 8 hours, or about 1 hour to about 12 hours.

In some embodiments, the sample is a non-biological sample. In some embodiments, the sample is sterile product, such as an eye drop or an ear drop. In some embodiments, the sample is an eye care product, such as a contact lens solution.

In some embodiments, the method further comprises identifying the pathogen. In some embodiments, identifying comprises comparing the colorimetric property of the sample to one or more positive controls containing known pathogen. In some embodiments, identifying comprises comparing the colorimetric property of the sample, or the pattern of nanoparticle association on the surface of the pathogen, to unique fingerprints for known pathogens. In some embodiments, the method is used for distinguishing between two or more different bacteria.

In some embodiments, the method further comprises quantifying the pathogen. In some embodiments, quantifying comprises comparing the colorimetric property of the sample to a standard curve. In some embodiments, quantifying comprises surface enhanced Raman spectroscopy.

In another aspect, there is provided method of identifying a pathogen comprising: a) contacting a sample suspected of containing a pathogen with a plurality of metallic nanoparticles under conditions suitable to permit association of the nanoparticles with the pathogen; and b) comparing a colorimetric property of the sample and/or the pattern of nanoparticle association on the surface of the pathogen to unique fingerprints for known pathogens. In some embodiments, the nanoparticles comprise a mixture of two or more distinct populations of nanoparticles. In some embodiments, the colorimetric property is UV-Visible absorbance. In some embodiments, the pattern of nanoparticle association on the surface of the pathogen is assessed using transmission electron microscopy (TEM).

In another aspect, there is provided a "fingerprint" of a known pathogen created based on a colorimetric property of a sample containing the known pathogen when exposed to a plurality of metallic nanoparticles under conditions suitable to permit association of the nanoparticles with the pathogen and/or created based on the pattern of nanoparticle association on the surface of the pathogen. Such fingerprints are useful in identifying an unknown pathogen in a sample. In some embodiments, the nanoparticles comprise a mixture of two or more distinct populations of nanoparticles. In some embodiments, the colorimertric property is UV-Visible absorbance. In some embodiments, the pattern of nanoparticle association on the surface of the pathogen is assessed using transmission electron microscopy (TEM). In some embodiments, the unknown pathogen is a bacterium.

In another aspect, there is provided, a kit for the direct detection of pathogen in a sample comprising: a container for receiving a sample suspected of containing a pathogen; a plurality of unmodified metallic nanoparticles; optionally, a liquid for suspending the nanoparticles prior to mixing with the sample; and instructions for carrying out the method.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Figure 1:
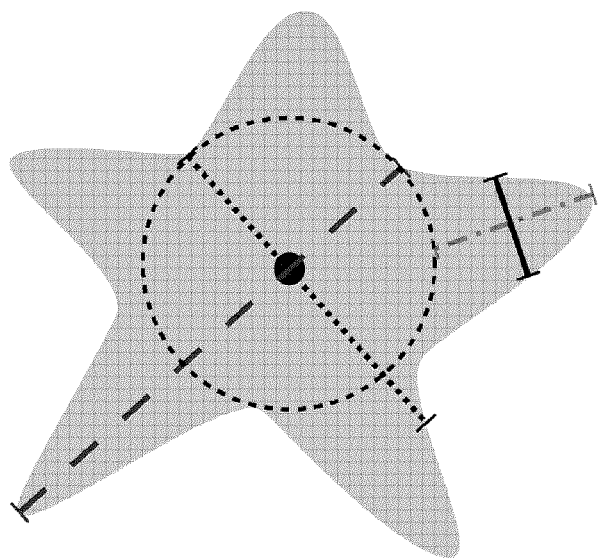
FIG. 1. Definition of various parameters for characterizing a gold nanostar. Total diameter is the maximum length of line segment that passes through the center of the star; Minor diameter is the minimum length of the line segment that passes through the center of the star; branch length is the distance from the tip of the branch to the expected curvature of the star core; branch width is the width measured at half the branch length.

The present disclosure relates to a method for the direct detection of pathogen in a sample using unmodified metallic nanoparticles. In some embodiments, the method is a colorimetric detection method. The combination of unmodified metallic nanoparticles and colorimetric detection provides a method that is simple, rapid and economical compared to prior art methods that require modified nanoparticles or expensive detection equipment. Moreover, the method does not require labeling of the target pathogen and is capable of detecting a broad spectrum of pathogens.

The term "metallic nanoparticle", as used herein, refers to particulate matter composed of metal atoms and having a particle size less than about 1000 nm in at least one dimension. Metallic nanoparticles may include, but are not limited to nanoparticles composed of gold, silver, copper, zinc, aluminum and platinum. In some embodiments, the metallic nanoparticles are gold or silver nanoparticles. In some embodiments, the metallic nanoparticles are gold nanoparticles.

Gold nanoparticles exhibit surface plasmon resonance, which is useful in their colorimetric detection. Small monodisperse gold nanoparticles causes an absorption of light in the blue-green region of the spectrum (~520 nm) while red light (~700 nm) is reflected, yielding a rich red color. As particle size increases, the wavelength of absorption shifts to longer wavelengths. Red light is then absorbed, and blue light is reflected, yielding solutions with a blue or purple color. The surface plasmon resonance can be tuned by varying the size or shape of the nanoparticles, leading to particles with tailored optical properties.

The term "unmodified", as used herein, means that the nanoparticles have not undergone surface modification, such as functionalization or conjugation to a target-specific ligand or label, in order to carry out the detection method. A skilled person will be familiar with various methods of modifying nanoparticles and will therefore readily understand the meaning of unmodified. Use of unmodified gold nanoparticles in colorimetric detection methods is described, for example, in Sha et al, 2011.

Metallic nanoparticles can be formed in many different shapes and sizes according to methods known to those skilled in the art (Xiao and Qi, 2011; Sun and Xia, 2002), as well as the exemplary methods disclosed herein. One exemplary method for forming gold nanoparticles is a two-step method involving seed-mediated growth. In a first step, spherical seed particles are generated using sodium citrate as a stabilizer and sodium borohydride as a strong reducing agent for the gold ions in solution. The formation of nanoseeds can be visualized since the solution turns a pale red color as the nanoseeds form. In the second step, L-ascorbic acid is used as a weak reductant and cetyltrimethylammonium bromide (CTAB) is used as a shape-templating surfactant to grow the seeds into larger particles of desired size and morphology in a solution of gold salt. Anisotropic growth of non-spherical nanoparticles, such as nanostars, may be encouraged using silver ions to create active sites where branching occurs. As the branched nanostars form, the solution turns from red to blue or purple depending on the size and morphology of the nanostars.

It will be understood that other surfactants could be used. For example, CTAB could be replaced with another surfactant from the same family as described by (Xiao and Qi, 2011). This family includes cetyltriethylammonium bromide, cetyltripropylammonium bromide, cetyltributylammonium bromide, cetylpyridin. The surfactant could also include those that have alkyl chains ranging from $C_{10}$ to $C_{20}$. Additionally bromide salts can be replaced with other halide salts such as chloride. A mixed system of surfactants can also be used, for example a combination of benzyldimethylhexadecylammonium chloride and CTAB.

It is demonstrated herein that the size and degree of branching of gold nanostars can be controlled by varying the amount of gold seed and/or the concentration of surfactant used in forming the nanoparticles, while keeping the concentration of silver nitrate, L-ascorbic acid and gold salt in solution constant. Increased gold seed volume results in smaller, more spherical, nanoparticles, while increased concentration of surfactant results in a higher degree of branching and longer branches.

The nanoparticles employed in the detection method may be any suitable shape or size that results in a detectable colorimetric response in the presence of pathogen, as may be determined by a skilled person. Exemplary nanoparticle shapes include, but are not limited to, nanospheres, nanostars, nanorods, nanocubes, nanoprisms, triangular and hexagonal nanoplates, nanocages, nanoshells, nanocapsules, dendritic nanoparticles, nanooctahedrons, nanocuboctahedrons, nanopyramids, nanodecahedrons, nanoisosahedron and nanowires.

In some embodiments, the nanoparticles are substantially spherical.

In some embodiments, the nanoparticles have branches (e.g. nanostars). In some embodiments, the nanoparticles have 1 to 20 branches, 1 to 15 branches, 1 to 10 branches, 1 to 9 branches, 1 to 8 branches, 1 to 7 branches, 1 to 6 branches, 1 to 5 branches, 1 to 4 branches, 1 to 3 branches, 1 to 2 branches. In some embodiments, the nanoparticles have 1, 2, 3, 4, 5, 6, 7, 8, 9, 10, 11, 12, 13, 14, 15, 16, 17, 18, 19 or 20 branches.

When nanoparticles are substantially spherical in shape, their size is determined by their diameter. When nanoparticles have branches, their size is determined by their total diameter, e.g. the maximum length passing through the center to include potential branches (see FIG. 1). The size of nanoparticles may be measured using any method known in the art. In some embodiments, the size is measured manually from images, such as transmission electron microscopy (TEM) images of the nanoparticles.

Some nanoparticles, such as nanowires, have a very high aspect ratio and may reach sizes up to about 10 μM. Accordingly, in some embodiments, the nanoparticles are less than about 10 μM.

Many nanoparticles, including nanostars, will fall into the range of about 1 nm to about 1000 nm. In some embodiments, the nanoparticles are less than about 1000 nm. In some embodiments, the nanoparticles are less than about 500 nm, less than about 400 nm, less than about 300 nm, less than about 200 nm, less than about 150 nm, less than 100 nm, less than about 90 nm, less than about 80 nm, less than about 70 nm, less than about 60 nm, less than about 50 nm, less than about 40 nm, less than about 35 nm, less than about 30 nm, less than about 25 nm, less than about 20 nm, less than about 15 nm, less than about 10 nm, less than about 9 nm, less than about 8 nm, less than about 7 nm, less than about 6 nm, less than about 5 nm, less than about 4 nm, less than about 3 nm, less than about 2 nm, less than about 1 nm.

In some embodiments, the nanoparticles (including nanostars) are between about 1 nm and about 1000 nm, between about 10 nm and about 1000 nm, between about 1 nm and about 500 nm, between about 10 nm and about 500 nm, between about 1 nm and about 250 nm, between about 10 nm and about 250 nm, between about 1 nm and about 200 nm, between about 10 nm and about 200 nm, between about 1 nm and about 150 nm, between about 10 nm and about 150 nm, between about 1 nm and about 100 nm, between about 10 nm and about 100 nm, between about 1 nm and about 80 nm, between about 10 nm and about 80 nm, between about 1 nm and about 60 nm, between about 10 nm and about 60 nm, between about 1 nm and about 50 nm, between about 10 nm and about 50 nm, between about 1 nm and about 40 nm, between about 10 nm and about 40 nm, between about 1 nm and about 30 nm, between about 10 nm and about 30 nm, between about 1 nm and about 20 nm, between about 10 nm and about 20 nm, between about 1 nm and about 10 nm, between about 1 nm and about 5 nm, between about 1 nm and about 4 nm, between about 1 nm and about 3 nm, or between about 1 nm and about 2 nm.

It will be understood that a population of nanoparticles may not be entirely uniform (e.g. monodisperse or homogeneous). There may be some variability in the size and/or shape of nanoparticles in a particular population of nanoparticles. For example, where a particular size or size range is specified, it will be understood that at least a majority of the nanoparticles in the population will have the specified property. Similarly, where a particular degree of branching is specified, it will be understood that at least a majority of the nanoparticles in the population will have the specified property. The term "at least a majority" typically means at least about 70%, at least about 80%, at least about 90%, or even about 100% for highly monodisperse populations (e.g. about 70%-100%, about 80%-100%, about 90%-100%, or about 100%).

In some embodiments, a plurality of nanoparticles may comprise a mixture of two or more populations of distinct nanoparticles of different shapes and/or sizes. In some embodiments, a plurality of nanoparticles may comprise two or more (e.g. 2, 3, 4, 5, 6, 7, 8, 9, 10, or more) distinct populations of nanoparticles. In some embodiments, a plurality of nanoparticles may comprise two distinct populations of nanoparticles. In some embodiments, a plurality of nanoparticles may comprise three distinct populations of nanoparticles. In some embodiments, a plurality of nanoparticles may comprise four distinct populations of nanoparticles. In some embodiments, a plurality of nanoparticles may comprise five distinct populations of nanoparticles. Distinct populations of nanoparticles may associate differently with the surfaces of different pathogens to thereby create a unique colorimetric response that can serve as a "fingerprint" to identify a pathogen.

A solution containing gold nanoparticles will range in color depending on the size and shape of the nanoparticles in the solution and the degree of aggregation of the particles. Aggregation of un-aggregated gold nanoparticles in solution leads to a color change. The optimal size and shape of the nanoparticles employed in the method can be determined by a person skilled in the art and may be selected based on, for example, a desired color difference in the presence versus the absence of pathogen. It could also be determined based on the specificity required to distinguish between different species of the pathogen.

Alternatively, the nanoparticles could be modified with ionic molecules which serve the same purpose as the unmodified nanoparticles, i.e. allow electrostatic interactions with the bacteria. Such nanoparticles should still perform in the same manner as the unmodified nanoparticle, but they may require surfactants in solution.

It is demonstrated herein that unmodified gold nanoparticles are capable of directly associating with the surface of pathogens. The pathogens themselves do not require any modification. The methods disclosed herein are believed to be useful for detecting a broad spectrum of pathogens. This provides an advantage over prior art methods that detect only a specific target pathogen (e.g. detecting target-specific DNA).

As used herein, "pathogen" refers to a microorganism, such as a bacterium, virus, fungus, protozoan or prion, whose surface is capable of associating with unmodified gold nanoparticles, as described herein. Without being bound by theory, it is believed that gold nanoparticles associate with the surface of pathogens, at least in part, via electrostatic interaction with polyanionic residues present on the surface of pathogens.

In some embodiments, the pathogen is a pathogen that is tested for in a hospital or clinic setting. In some embodiments, the pathogen is a pathogen that is tested for in the environment, such as water contamination. In some embodiments, the pathogen is a pathogen that is tested for in medical products, such medicines and medical-grade solutions. In some embodiments, the pathogen is a pathogen that is tested for in a laboratory. In some embodiments, the pathogen is a pathogen that is tested for in consumer goods. In some embodiments, the pathogen is a pathogen that is tested for in foods, including beverages. In some embodiments, the pathogen is a pathogen that is tested for in cosmetic products.

In some embodiments, the pathogen is a bacterium. As demonstrated herein, the method can be used to detect a broad spectrum of bacteria, including Gram-positive and Gram-negative bacteria. Interestingly, gold nanoparticles were found to associate differently with the surfaces of different bacteria, thereby providing a unique "fingerprint" that can be used to distinguish between different bacteria. The "fingerprint" may be a unique colorimetric response (e.g. a unique UV-Visible absorption spectra) or it may be a unique pattern of nanoparticle association on the surface of a pathogen (e.g. visible in transmission electron microscope (TEM) images).

In some embodiments, the bacterium is selected from *Staphylococcus aureus, Streptococcus pneumoniae, Enterococcus faecalis, Achromobacter xylosoxidans, Escherichia coli, Delftia acidovorans, Pseudomonas aeruginosa, Serratia marcescens, Stenotrophomonas maltophilia, Amycolatopsis azurea, Amycolatopsis orientalis, Bacillus lichenformis, Bacillus subtilis, Lactococcus lactis, Lactobacillus plantarum, Pseudomonas putida, Streptomyces coelicolor, Streptomyces griseus, Shewane/la oneidensis, Vibrio fischeri, Vibrio alginolyticus, Micrococcus luteus, Pichia pastoris, Edwardsiella tarda, Elizabethkingia meningoseptica, Salmonella typhi, Salmonella typhimurium, Salmonella enterica, Staphylococcus epidermis, Kelbsiella pneumoniae, Bacillus cereus, Mycobacterium tuberculosis, Acinetobacter baumannii, Helicobacter pylori, Listeria monocytogenes, Bacillus anthracis, Chlamydia trachomatis, Neisseria gonorrhoeae, Treponema pallidum, Campylobacter jejuni, Legionella pneumophila, Haemophilus influenza,* or *Clostridium difficile.*

In some embodiments, the bacterium is selected from *Staphylococcus aureus, Streptococcus pneumoniae, Enterococcus faecalis, Achromobacter xylosoxidans, Escherichia coli, Delftia acidovorans, Pseudomonas aeruginosa* and *Stenotrophomonas maltophilia.*

In some embodiments, the bacterium is *Staphylococcus aureus*. In some embodiments, the bacterium is *Streptococcus pneumonia*. In some embodiments, the bacterium is *Enterococcus faecalis*. In some embodiments, the bacterium is *Achromobacter xylosoxidans*. In some embodiments, the bacterium is *Escherichia coli*. In some embodiments, the bacterium is *Delftia acidovorans*, In some embodiments, the bacterium is *Pseudomonas aeruginosa*. In some embodiments, the bacterium is *Stenotrophomonas maltophilia.*

In some embodiments, the pathogen is a virus. In some embodiments, the virus is selected from penaeus vannamei nodavirus, white spot syndrome virus, infectious myonecrosis virus, influenza H1N1 virus, human immunodeficiency virus, human papillomavirus, hepatitis A virus, hepatitis B virus, hepatitis C virus, dengue virus, Kaposi's sarcoma associated herpesvirus, peste des petits ruminants virus, plum pox virus, Gemini virus, Newcastle disease virus, herpes simplex virus, varicella-zoster virus, picornavirus, and poxvirus.

In some embodiments, the pathogen is a protozoan. In some embodiments, the protozoan is selected from *Leishmania, Acanthamoeba, Entamoeba, Giardia, Plasmodium* or *Trypanosoma.*

In some embodiments, the pathogen is a fungus. In some embodiments, the fungus is selected from from *Candidia albicans, Aspergillus niger, Fusarium solani, Cryptococcus neoformans, Histoplasma capsulatum, Histoplasma capsulatum, Pneumocystis jirovecii, Stachybortrys chartarum, Bortiytis cinema,*

In some embodiments, the pathogen is a prion. In some embodiments, the prion causing transmissible spongiform encephalopathies.

The present disclosure provides a simple method for detecting the presence or absence of pathogen in a sample using unmodified metallic nanoparticles. The method may be a colorimetric detection method. Although gold nanoparticels are exemplified in the specification, a skilled person will appreciate that other metallic nanoparticles may also be used. In some embodiments, the method also allows for identification and/or quantification of the pathogen detected.

The method is based on the discovery that unmodified gold nanoparticles are capable of associating, e.g. interacting, with the surface of pathogens. This association leads to aggregation of the nanoparticles around the pathogen because the distance between nanoparticles is reduced as compared to the nanoparticles in solution in the absence of pathogen. The aggregation leads to a color change due to a shift in the surface plasmon resonance of the nanoparticles. This color change can then be detected. Thus, in the present method, a pathogen, when present, may be detected directly via aggregation of the nanoparticles on the surface of the pathogen. This is in contrast to various prior art methods that rely on indirect detection of a target using nanoparticles.

When there is a great deal of nanoparticle aggregation on the surface of pathogens, the number of nanoparticles remaining in solution, i.e. not aggregated, is significantly reduced—leading to a loss of color in the solution because of a change in the surface plasmon resonance of the gold nanoparticles. This is a unique property of noble metal particles: their surface plasmon resonance frequency changes upon aggregation because the particles are now coupled. This change in frequency causes a loss in the color because the nanoparticles do not absorb light in the visible region. This causes a loss of the UV-Visible absorption peak and is detectable as well as quantifiable. Thus, a sample containing pathogen will have a different color than a sample that is free of pathogen. Additionally, different pathogens have a unique number of nanoparticles associated on the surface, and the spacing of the particles may also differ, which leads to a unique colorimetric response (e.g. "fingerprint") that can be used to identify the pathogens.

The method generally comprises contacting a sample with a plurality of unmodified metallic nanoparticles under conditions suitable to permit association of the nanoparticles with the pathogen, if present, and assessing a colorimetric property of the sample to determine the presence or absence of the pathogen.

The assessing step may comprise comparing a colorimetric property of the sample to a corresponding colorimetric property of a suitable control and determining whether there is a difference between the sample and the control. The colorimetric property of the sample or control will depend at least in part on the relative amount of nanoparticles associated with the surface of pathogens (and their degree of aggregation) and the amount of nanoparticles remaining in the solution.

In one embodiment, there is provided a colorimetric method for detecting a pathogen in a sample, which comprises: a) contacting a sample suspected of containing a pathogen with a plurality of unmodified metallic nanoparticles under conditions suitable to permit association of the nanoparticles with the pathogen, if present; b) assessing a colorimetric property of the sample; and c) comparing the colorimetric property of the sample to a control. The method may further comprise the active step of making a determination of the presence or absence of pathogen.

A colorimetric property (e.g. color) of a sample or a control may be determined according to various colorimetric methods known in the art.

In some cases, the color may be visually detected with the naked eye. The color difference may be assessed between a sample and a separate control, or the color change may be observed as a change in the sample over time wherein the original sample serves as its own control. In other cases, the colorimetric property may be assessed spectrophotometrically, for example, with a UV-Visible spectrophotometer or a diffuse reflectance spectrometer. The color could also be measured by capturing a photograph using a digital camera and then performing image analysis.

The colorimetric property of a sample compared to a control (or a sample relative to another sample, or a control relative to another control) may, for example, be assessed by comparing the UV-Visible absorbance of different solutions. In some embodiments, absorption spectra may be obtained by measuring absorbance across a range of relevant wavelengths, for example, from about 300 nm to 900 nm. The measurements are taken at intervals, for example, a step size of about 0.1-10 nm may be employed, e.g. 1 nm. The colorimetric property may be assessed based on one or more parameters of the absorbance spectra, including but not limited to, peak absorbance wavelength (nm), peak height and/or peak width. One exemplary parameter that may be assessed is the Full Width Half Maximum (FWHM) of the absorbance spectra, which can easily be calculated.

The colorimetric property of the sample may be compared to that of a negative control, a positive control, or both, in order to make a determination. A negative control is one that is substantially free of pathogen. A positive control is one that contains a pathogen. As a skilled person will appreciate, controls are typically provided in a solution that mimics (i.e. substantially similar or the same) the sample solution.

A difference in the colorimetric property of the sample compared to a negative control indicates the presence of pathogen whereas a similarity in the colorimetric property of the sample compared to a negative control indicates the absence of pathogen. Conversely, a similarity in the colorimetric property of the sample compared to a positive control indicates the presence of pathogen. A sample may also be compared against a standard curve prepared from positive controls containing different amounts of a known pathogen or to a library of controls (e.g. a training set) containing known pathogens. The comparison is preferably in reference to a positive or negative control that is run at the same time the sample is tested but it may also be based on a historical control. In some cases, the control may be the sample itself at an earlier time point. For example, where a visual difference in a solution occurs when the solution becomes contamination, the control may be the same solution prior to the contamination, or it may be a reference solution that is not contaminated. In this way, the method can be used to visually detect the shelf-life of products. Positive and negative controls may sometimes be used simply to ensure that the method is working properly.

The step of assessing the colorimetric property of a sample compared to a control may include determining whether there is a "significant" difference between the sample and the control. An appropriate degree of significance can be determined by a skilled person.

Although a colorimetric detection method is exemplified herein, the method is not limited to colorimetric detection. In some cases, the association of nanoparticles can be assessed using infrared radiation, microwave radiation, terahertz radiation, and radio waves. This is possible by spectroscopic methods utilizing the respective electromagnetic spectrum, for example Fourier transform infrared spectroscopy, Fourier transform microwave spectroscopy, terahertz spectroscopy or radio-frequency spectroscopy. It is expected that the spectra in these regions will also show unique characteristics for each pathogen of interest.

The information obtained from the comparisons performed can be used to make a determination of the presence or absence of pathogen in the sample. In some cases, the determination can be made visually or manually. In some cases, software may be employed.

A skilled person can determine suitable conditions for use in the methods of the present disclosure, such that every detail need not be described herein.

In carrying out the method, a sample is contacted with a plurality of nanoparticles under conditions suitable to permit association of the nanoparticles with the pathogen, if present. Typically, the nanoparticles will be added to, or provided in, a suitable liquid, such that they are free to move around and interact with the surface of any pathogens that they encounter. As the nanoparticles associate with pathogens, the distance between adjacent nanoparticles may decrease such that aggregation occurs on the surface of the pathogen.

The liquid may contain a surfactant, such as CTAB. The surfactant may assist in limiting, or inhibiting, non-specific aggregation of the nanoparticles in the liquid (e.g. aggregation that is not due to interaction with pathogen). In some embodiments, the liquid contains between about 0.1 mM-about 100 mM CTAB, 0.1 mM-about 10 mM CTAB, 0.5 mM-about 5 mM CTAB, 0.5 mM-about 2 mM CTAB, 0.1 mM-about 1 mM, or about 1 mM CTAB.

The liquid may comprise one or more agents that further limit or inhibit non-specific aggregation of the nanoparticles in the absence of pathogen. Such agents may include, for example, a polysaccharide, polyethylene glycol or a derivative of polyethylene glycol, an alkanethiol, an amino acid or a derivative of amino acid, a protein or a polynucleotide.

In some cases, the sample is mixed with a liquid containing the nanoparticles. In some cases, the nanoparticles are added to a liquid (e.g. a sample) suspected of containing pathogen. In some cases, the sample is a liquid product containing nanoparticles, wherein the colorimetric property of the liquid changes upon contamination with pathogen.

The nanoparticles should remain in contact with the sample for a sufficient amount of time to allow the nanoparticles to associate with pathogen, if present, and potentially aggregate on the surface of the pathogen depending on their proximity to one another. In some cases, the association may occur rapidly. In other cases, a longer contact period may be needed. A suitable time period may be determined by the skilled person. In some embodiments, the contact period may be at least 5 seconds, at least 10 seconds, at least 30 seconds, at least 1 minute, at least 5 minutes, at least 10 minutes, at least 30 minutes, at least 1 hour, at least 5 hours, at least 8 hours, at least 12 hours, or more. In some embodiments, the contact period is a range of about 5 seconds to about 12 hours, about 10 seconds to about 1 hour, about 10 seconds to about 10 minutes, about 1 minute to about 1 hour, about 1 hour to about 8 hours, or about 1 hour to about 12 hours. Association may be aided in some cases, by stirring, mixing or the like.

A skilled person will be able to determine optimal reactions conditions, including but not limited to concentration of components, pH, temperature, and time.

The detection method may further comprise a step of identifying and/or quantifying the pathogen. In some embodiments, the method further comprises identification of the pathogen. In some embodiments, the method further comprises quantification of the pathogen. In some embodiments, the method further comprises identification and quantification of the pathogen.

The step of identifying the pathogen may be performed according to any method known in the art. In one embodiment, the step of identifying the pathogen comprises comparing the colorimetric property of a sample solution comprising the pathogen to one or more controls containing known pathogen. In some cases, the sample may be compared against a library of controls containing known pathogens.

It is demonstrated herein that gold nanoparticles associate differently with the surfaces of different pathogens to provide unique colorimetric responses, likely due to the unique surface characteristics of different pathogens. The use of a mixture of two or more distinct populations of nanoparticles (e.g. having a different shape and/or size from each other) can further increase uniqueness of the colorimetric response, such that "fingerprints" can be created to identify various pathogens. In some embodiments, the method employs two or more distinct populations of nanoparticles (e.g, 2, 3, 4, 5, 6, 7, 8, 9, 10 or more).

In some embodiments, the step of identifying the pathogen includes examining the pattern of nanoparticles associated with the surface of the pathogen, for example, using transmission electron microscopy (TEM). It is demonstrated herein that unique patterns of association are created, again, serving as a "fingerprint" to identify pathogens. For example, even if two pathogens look quite similar in size and shape under a microscope, the manner in which nanoparticles associate with the surfaces of the two pathogens is unique and can be used to differentiate the pathogens.

In some cases, the method may be used to identify an unknown pathogen in a sample. In some cases, the method may be used to identify the type of pathogen in a sample (e.g. bacteria, virus, protozpan, fungus, prion). In some cases, the method may be used to differentiate between two or more species, genus, subgenus or strains of a pathogen, such as bacteria.

The step of quantifying the pathogen may be performed according to any method known in the art. In some embodiments, the step of quantifying comprises comparing the colorimetric property of a sample against a standard curve prepared using known amounts of pathogen, either by comparing visually by the naked eye, using a digital camera or by using ultraviolet-visible absorption spectroscopy. In some embodiments, the step of quantifying involves surface enhanced Raman spectroscopy. In some embodiments, the step of quantifying involves fluorescence spectroscopy.

The method can comprise additional steps, including but not limited to, providing one or more control reactions, for example, to determine whether one or more steps in the method have been performed successfully, to determine whether one or more components is functioning as expected, or to determine if substances that interfere with the ability of the method to generate reliable results are present in the sample. Such control reactions are well-known to those of skill in the art, and their design and implementation need not be detailed herein. The method may also comprise one or more steps, such as, adding an agent to limit or inhibit non-specific aggregation of the nanoparticles in solution, removal of undesirable components, dilution or concentration steps, or preparation of a standard curve.

A "sample" is typically a liquid, such as a solution suspected of containing a pathogen. Any suitable solution may be used as a sample in the method. The term "solution" is used interchangeably with liquid, suspension or emulsion herein. The phrase "suspected of containing a pathogen" simply means that it is desirable to determine the presence or absence of a pathogen. The sample may, for example, be a final product, such as clean or sterile product, such as a consumer product or a food product, wherein it is desirable to know if the product has become contaminated with a pathogen.

A sample may be a portion of a solution that is aliquoted for testing in the method, or it may be an undiluted liquid product, such as a consumer product on the shelf. The sample may be provided in the form that it was obtained (e.g. a consumer product, a food product, a medicine, blood, urine, drinking water, or lake water). Alternatively, the sample can be treated to remove one or more undesirable components or to isolate or concentrate the pathogen, if present. This can be performed by centrifugation such that the pathogen precipitates and the interferents remain in the supernatant. It could also be done by filtration with the membrane pore size of <500 nm, such that the pathogens are retained on the membrane and the undesired components remain in the solution. For example, the nanoparticles could then be added to the membrane retentate.

Where necessary, the amount or concentration of the pathogen to be detected in the sample, can be adjusted to achieve satisfactory detection. Adjustment can be accomplished, for example, by dilution or concentration of the sample. Dilution may be made with any compatible liquid. Any suitable concentration technique may be employed, including but not limited to, centrifugation, filtration, evaporation, lyophilization, purification, or the like.

Additional components may also be added to the sample prior to, or at the time of, testing the sample. Additional component may include any components that do not render the sample incompatible for use in the method. Examples may include salts, polymers, surfactants, solvents, preservatives, proteins and nucleic acids.

Other handling or manipulation of the sample can be performed prior to or at the time the method is carried out. Any handling or manipulation may be used as long as it does not render the sample incompatible for use in the method.

A sample may start out as a liquid or it may be derived from a solid or semi-solid starting material, for example, by addition of a liquid to give it a liquid characteristic suitable for use in the method.

In some embodiments, the sample is a "biological sample", such as blood or a portion of blood, urine, feces, saliva, sputum, tear fluid, mucous, semen, or homogenized tissue. In some embodiments, the sample is a biological sample that has been treated to remove components that would interfere with the method.

In some embodiments, the sample is a "non-biological sample", meaning that the sample that was not obtained from a living organism. Such samples are particularly contemplated in the methods disclosed herein.

In some embodiments, the sample is a sterile product. By "sterile product" it is meant that the product is intended to be sterile in use. It is often desirable to determine whether a sterile product has become contaminated with pathogen. Examples of sterile product may include, for example, a consumer product (e.g. contact lens solution), a medicine (e.g. eye or ear drops, injectables), a medical-grade product (e.g. sterile saline solution, implants), a laboratory product (e.g. sterile cell culture products), or sterile water. In some embodiments, the sample is sterile consumer product, such as a contact lens solution. In some embodiments, the sample is a sterile medicine, such as an eye or ear drop.

In some embodiments, the sample is a non-sterile product. By "non-sterile" it is meant that the product does not need to be completely free of microorganisms in use. A certain level or type of microorganism may be tolerated. However, it may be desirable to determine whether the product contains a pathogenic microorganism or whether a product exceeds a tolerated threshold of microbial contamination.

In some embodiments, the sample is a non-sterile consumer product.

In some embodiments, the sample is a sterile or non-sterile food product. A food product may include, for example, solid, semi-solid or liquid food products. In some embodiments, the liquid food product is a beverage, such as a packaged consumer beverage (e.g. bottle, can, tetra-pack, bag).

In some embodiments, the sample is water. Water may include, for example, drinking water, process water, distilled water, river water, steam water, lake water, ocean water, and the like. In some embodiments, the sample is drinking water, such as tap water or bottled water. In some embodiments, the water is sterile water.

A kit refers to a composition of matter containing one or more components necessary to practice the method of detecting a pathogen using unmodified metallic nanoparticles, such as gold nanoparticles. In some embodiments, the kit comprises unmodified metallic nanoparticles or a mixture of two or more populations of nanoparticles and optionally a reagent to serve as control. The nanoparticles may be provided in a solid or a liquid form. For example, they may be provided in a container to which liquid is added. Or the kit may comprise a liquid containing the nanoparticles in solution. The nanoparticles may be in the form of a strip made of material, such as paper, such that the strip could be immersed in a suitable suspension liquid or directly in a sample. The kit may also contain a container for mixing of the nanoparticles with a sample and/or mixing of the nanoparticles with a control. The kit may contain a container, such as a multi-well plate, for assessing multiple samples. The kit may contain a buffer or other suitable solution. A kit may contain one or more of a solution in which gold nanoparticles and the sample are mixed, a negative control, a positive control, one or more reaction containers, such as tubes or wells, a colorimetric chart, a packaging material, an instruction for use in detecting a pathogen.

The present disclosure provides a method of detecting pathogens that is simple, rapid and economical. A skilled person will recognize that there are many potential applications for such a method. Applications are not limited to the examples below.

In one aspect, the method may be used to assess the shelf-life of products. For example, a sample may be taken from the product and tested in the method to determine whether contamination with a pathogen has occurred. In some cases, the product itself may contain nanoparticles such that a colormetric change can be detected if the product becomes contaminated. In some cases, this may be observed as a visible color change in the solution. Numerous products are contemplated, including various consumer goods, eye care products, medicines, medical products, laboratory products, and foods, including beverages, among others. In some cases, the product is a clean or sterile product.

In another aspect, the method may be used in a clinic or hospital setting. The method may be used, for example, as a rapid point-of-care method for detecting a pathogen, identifying a pathogen, quantifying a pathogen, or for discriminating between two or more pathogens. For example, the method may be used to quickly distinguish between a bacteria and a virus so that appropriate prescription medication can be prescribed at a clinic. A simple point-of-care diagnostic relying on the method of the present disclosure could reduce the number of antibiotics inappropriately prescribed for viral infections. In order to be certain an infection is bacterial, a doctor must currently send a sample off to a lab for analysis and the results take days. The doctor will often prescribe an antibiotic prescription just in case the result is positive. Accordingly, the method disclosed herein may include an additional step of prescribing a medication upon detection and/or identification of a pathogen. For example, the medication may be and antibiotic, such as vancomycin hydrochoride, or ay cell wall-binding molecult. The medication may be an antifungal, such as amphotericin B or natamycin.

Once particularly contemplated application is eye care products, such as contact lens solutions, contact lens cases, or eye drops. In some cases, the method may be used to diagnose an eye infection. Contact lens wear increases the risk of microbial keratitis, which can lead to blindness. In order to treat the ocular infection effectively, it is important to identify the strain responsible. Current methods require several days for the determining the identity of bacteria, which can lead to incorrectly prescribed antibiotics and prolong treatment. The method may also be used to detect changes in pH or salt concentration in eye care products, which could lead to eye irritation.

It is also contemplated that the method could be employed in a laboratory setting, such as a research lab or a hospital lab. The method could be used to detect contamination in various laboratory products or could be employed in the course of research to detect, identify and/or quantify pathogens.

It is also contemplated that the method could be employed in environmental applications, such as detection of pathogens in a water source, such as drinking water, lake water, river water, stream water, ocean water, treatment water or process water. The method could also be used recreationally, for example, to quickly test whether a source of drinking or cooking water is contaminated while camping or hiking.

The method could be used in a portable strip type detector such that the strip is immersed in an environmental sample in the field. The method could be used at the point-of-care where the sample is a contaminated product such as contact lens, contact lens case, implant, ornaments, clothes. The method could be used by consumers in their home if they wish to find out if a certain area of the house is contaminated by pouring the solution in that area. It could be used in hospitals on keyboards since that is a source of transmitting diseases. The method can be used in research labs to discover new strains of bacteria if their response is not comparable to any of the controls. The method could be used to understand the interactions between cells and nanoparticles and hence design new biosensors. The method can be used to understand the composition of cells. It is also contemplated that the method could be used to distinguish between pathogenic and non-pathogenic contaminants.

The term "about", when used in connection with numerical values, is intended to include a range about the stated value of 5% at either end of the recited number. Thus, e.g., about 100 nm includes a range of 95 nm to 105 nm.

In some embodiments disclosed herein, the steps in a method are referred to using letters for convenience. The letters do not necessarily imply that the steps must be performed in the specified order. In some cases, two steps may occur simultaneously, such as association of nanoparticles on the surface of pathogen and their aggregation with one another. A skilled person will be able to determine the appropriate sequence of the steps.

EXAMPLES

Example 1: Synthesis and Characterization of Gold Nanoparticles

Materials and Methods
Synthesis of Gold Nanoseed.

Gold (III) chloride hydrate, silver nitrate, cetyl trimethylammonium bromide (CTAB), sodium borohydride and L-ascorbic acid were purchased from Sigma-Aldrich. Sodium citrate dihydrate was purchased from Fisher Scientific. A gold and citrate solution was prepared by adding 1.88 mg gold (III) chloride hydrate salt and 0.58 mg sodium citrate dehydrate to 20 mL of Millipore water. A solution of sodium borohydride was prepared by adding 3.78 mg sodium borohydride to 1 mL of cold Millipore water. This solution was kept cold by keeping the container in an ice bath. Once the sodium borohydride dissolved, 60 μL of the solution was added to 20 mL of the gold solution under stirring. The color of solution quickly turned brownish pink. After one minute of stirring, the stir bar was extracted and the solution was left undisturbed at room temperature overnight in the dark. The solution of gold turned red indicating the formation of gold nanoseeds. This solution was filtered using a 200 nm filter and stored in the refrigerator until further use.

Synthesis of Gold Nanostars.

A solution of CTAB was prepared by the addition of 50 mg CTAB to 46.8 mL of Millipore water and then placing the solution in a water bath at 60° C. A solution of gold salt was prepared by adding 11.3 mg gold (III) chloride hydrate to 3 mL Millipore water. A solution of silver nitrate was prepared by the addition of 1.69 mg silver nitrate salt to 1 mL Millipore water. A solution of L-ascorbic acid was prepared by addition of 17.6 mg L-ascorbic acid to 1 mL Millipore water. All salts were dissolved by vortexing. Next, 2 mL of gold salt solution was added to the CTAB solution under magnetic stirring which gave the solution a brownish-orange color. This was followed by addition of 0.3 mL of silver nitrate solution. Next, 0.32 mL of Ascorbic acid solution was added in a dropwise manner and the solution turned colorless. Finally, 0.5 mL of gold nanoseeds from example 1 were added to the solution, which changed the color to blue within two minutes indicating the formation of gold nanostars. The stir bar was removed and gold nanostars were stored in the dark at room temperature until further use.

Synthesis of Gold Nanostars with Different Shapes and Sizes.

The shape and size of gold nanostars was changed by changing the CTAB and seed amounts. The reaction was scaled down from 50 mL to 16 mL final volume. The following mass of CTAB were added to 50 mL of Millipore water: 25 mg, 75 mg, 100 mg, 125 mg in addition to the 50 mg that was used above. The addition of 0.5 mL of gold nanoseed in 50 mL is equivalent to 160 μL in 16 mL. For each CTAB concentration, the seed volume was changed to 32 μL, 80 μL, 160 μL, 240 μL, 320 μL and 400 μL while keeping the volume of the varying CTAB concentration solution consistent. This provided a total of 30 different compositions of gold nanostars.

TEM samples were prepared by placing 5 μL of each gold nanostar on a 300 mesh Formvar coated copper grid (Canemco & Merivac) and letting the sample dry overnight. The nanostars were then imaged using a Philips CM10 Transmission Electron Microscope. These images are presented in FIG. 2.

Figure 4:
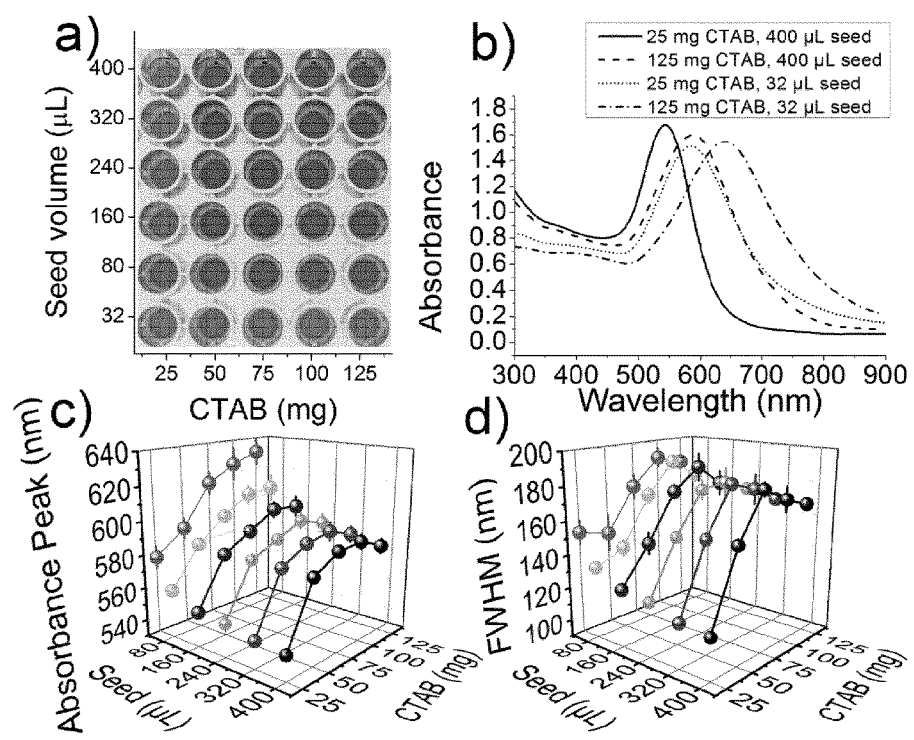
FIG. 4. Optical properties of gold nanostars. a) Photograph showing the color of gold nanostars b) UV-Visible absorption spectra for four of the gold nanostars with varying seed and CTAB concentrations. Effect of CTAB and seed concentrations on c) UV-Visible absorbance peaks (n=6, mean±S.D.), and on d) Full Width Half Maximum (FWHM) (n=6, mean±S.D.).

The nanostars were also characterized using UV-Visible spectroscopy using a Biotek Epoch Multi-volume Spectrophotometer System. A spectral scan from 300 nm to 900 nm was conducted with a step size of 1 nm in duplicates. The absorbance peak was determined and average was measured over three different replicates. These results are presented in FIG. 4.

Results and Discussion

Gold nanostars were synthesized at room temperature via a seed-mediated growth mechanism using cetyltrimethylammonium bromide (CTAB) surfactant as a template (Lu et al., 2010). The mechanism of anisotropic growth in gold nanoparticles is currently being investigated and often the growth of gold nanostars is compared to that of gold nanorods, because both morphologies use CTAB surfactant as a negative template and silver ions for creating active sites (Sau and Rogach, 2010; Wu et al., 2009; Grzelczak et al., 2008; Nehl et al., 2006; Chen et al., 2005). In the case of nanostars, the twin defects on the surface of the seed are postulated to weaken the binding of the positively charged CTAB surfactant, which allows the growth of branches at these sites (Nehl et al., 2006). Also, silver can be deposited on the surface of the seed by underpotential and produce additional defects, which in turn act as active sites for growth of branches. (Sau and Rogach, 2010; Min-Chen et al., 2009; Nehl et al., 2006) We hypothesize that the surface morphology and particle size of gold nanostars can be controlled by changing the amount of gold seed precursor (32, 80, 160, 240, 320 or 400 µL) and CTAB (25, 50, 75, 100, 125 mg) added to the formulation. To test this hypothesis, we synthesized 30 types of gold nanostars by using all possible combinations of these two parameters, while keeping the amount of silver nitrate, L-ascorbic acid and gold salt in solution constant. These nanostars (FIG. 1) were characterized using transmission electron microscopy (TEM) to determine their size and surface morphology and using UV-Vis spectroscopy to determine their absorption spectra. We then demonstrated that the gold nanostars change color drastically in the presence of *S. aureus* as compared to a saline (2.55% with ~0.006% broth) control.

Figure 2:
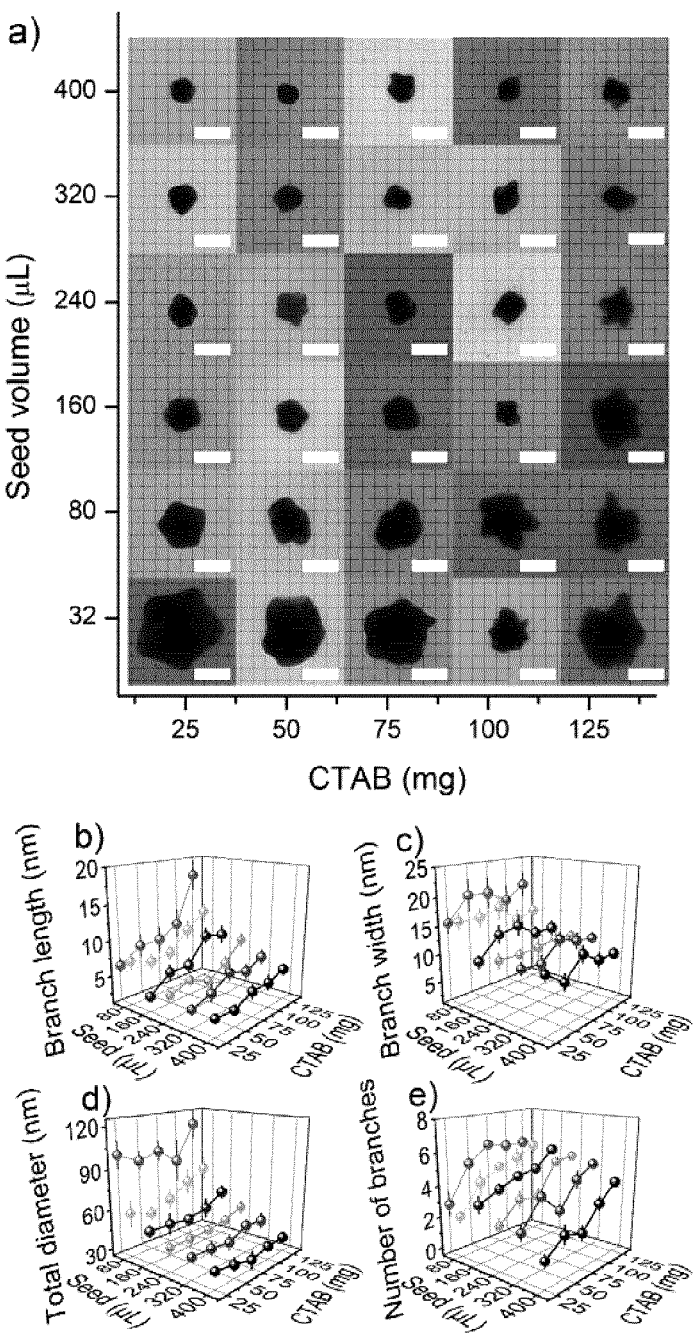
FIG. 2. Transmission Electron Micrographs (TEM) of Gold Nanostars. a) TEM images of thirty nanostar samples (scale bar: 50 nm). Various parameters defined in FIG. 1, measured from the TEM images for nanostars: b) Branch length (n=10; mean±S.E) c) Branch width (n=10; mean±S.E), d) Total diameter (n=10; mean±S.D.), e) Number of branches (n=10; mean±S.E.).
Figure 3:
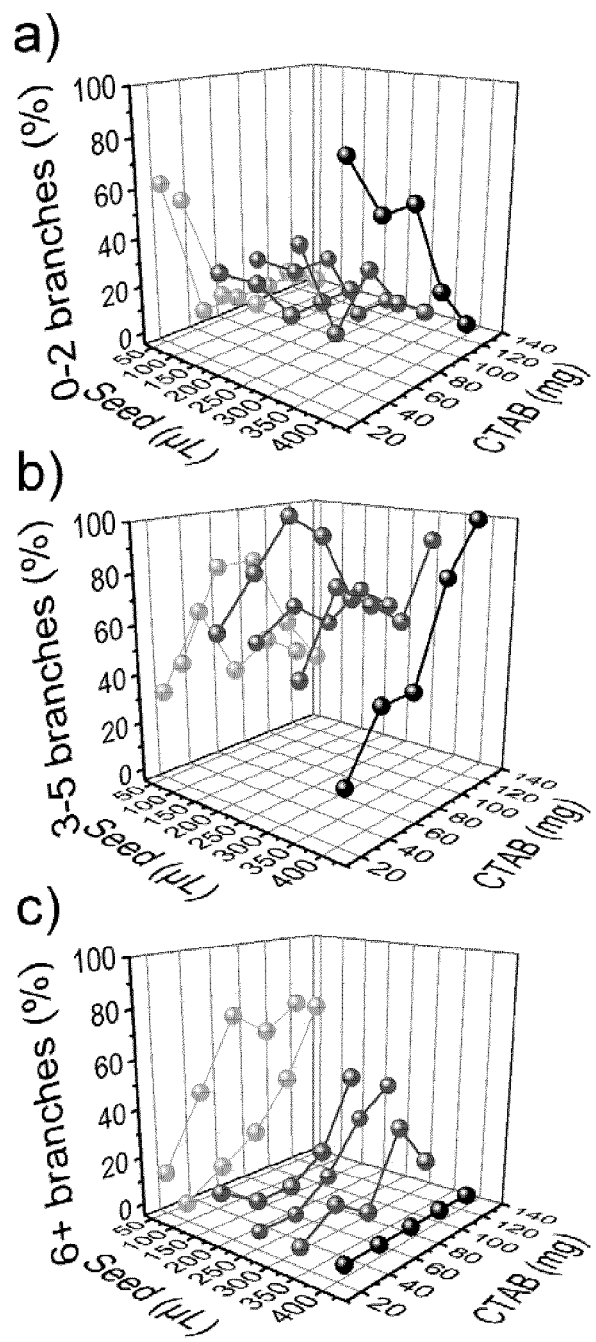
FIG. 3. Distribution of branches. The distribution of branches for the entire 30 nanostar set was characterized using TEM images, and is recorded above, corresponding to bins of a) 0-2 branches, b) 3-5 branches and c) 6+ branches.

The TEM images of the 30 samples of gold nanostars show that the total size of nanostars is mostly controlled by the amount of gold nanoseed added, while the degree of branching and branch length are controlled by the CTAB amounts (FIG. 2). Increasing the amount of seed decreases the total size because more growth sites are present and the total amount of gold available for growth in solution is kept constant. Increasing the amount of CTAB increases the branch length and the average number of branches because the number of CTAB micelles per seed increases. We quantified the size and degree of branching for each of the 30 samples by measuring the total diameter, branch length and branch width, as defined in FIG. 1 using National Institutes of Health software ImageJ. The total diameter and branch length (FIG. 2b, d) showed dependence on seed and CTAB concentration, as diametric and branch growth occurs simultaneously when gold is available in solution. This also leads to the relatively uniform growth of branch width under the same conditions as growth of the stars (FIG. 2c). The total diameter ranged from 31 nm to 113 nm for 400 µL and 32 µL seed sets respectively, while the length of branches ranged from 3 nm to 17 nm for 25 mg CTAB and 125 mg CTAB sets respectively (FIG. 2b, d). The changes in surfactant and seed not only affect the dimensions of the branches but also the average number of branches, which ranges from one to six (FIG. 2e). We believe this is because the higher concentration of CTAB per seed allows better adsorption of CTAB, which in turn promotes anisotropic growth at multiple sites. Additionally, the distribution of stars with increasing number of branches also varies with the amount of seed and CTAB. Low seed volumes and high concentration of CTAB are necessary for a higher fraction of highly branched nanostars (FIG. 3). Although there are some rare outliers in the TEM images of single nanostars due to the nature of selecting individual nanoparticles to image, the trends of size and branching are clearly visible in the images as well as the plots that follow in FIG. 2.

The color of gold nanoparticles is determined by the size of the particles because of their surface plasmon resonance. A change in the surface plasmon resonance of the particles can be characterized by the absorption peak of UV-Vis spectroscopy (Xia et al., 2010; Min-Chen et al., 2009; Wu et al., 2009; Nehl et al., 2006). As seen in FIG. 4a), varying size and the degree of branching yields nanostars with different solution colors. The lowest CTAB, highest seed sample yields a red color. This sample lacks significant branching and thus is found to have a more spherical morphology, as we previously described. Spherical gold nanoparticles have been extensively studied in the past, and as we observed, give the solution a distinct red color (Link and El-Sayed, 2000). Decreasing seed and increasing CTAB causes the gold nanostar solutions to be violet and then blue, resulting from a shift in plasmon resonances caused by increased degree of branching and general star-like morphology (Lu et al., 2010; Hao et al., 2007). The dependence of absorption peak and width on the degree of branching has rarely been explored (Yuan et al., 2012). We repeated the synthesis of the 30 stars three times and measured the absorption spectra from 300 nm to 900 nm with a step size of 1 nm. As an example, we plotted the complete spectra of the four extreme synthesis data samples (FIG. 4b). We also extracted the peaks and full width half maximum values (FWHM) from the spectra of all the nanostars (FIG. 4c,d). Increasing size of the nanostars by decreasing seed leads to a red shift in the absorption peak and also broadens the width. Additionally, there is a significant jump in the peak and FWHM when increasing the CTAB from 25 to 50 mg even though the size of the particles only varies slightly. This jump suggests that a minimum concentration of CTAB is necessary for changing the morphology of nanoparticles from spheres to stars and causing a shift in absorbance peak of about 60 nm (Lu et al., 2010). Interestingly, a characteristic drop in the peak position and FWHM occurs at the highest CTAB concentration for all seed volumes when the number and length of branches is the highest. This drop is in agreement with previously modeled data, where a slight blue shift in absorbance peak is observed when the number of branches was increased from four to ten (Yuan et al., 2012). The drop in the FWHM at highest CTAB concentration also suggests that the size distribution of nanostars is narrower (Yuan et al., 2012). This is most likely because a higher concentration of CTAB allows for more homogenous adsorption of CTAB on the seeds, thereby synthesizing more monodisperse gold nanostars.

Example 2: Detection of *Staphylococcus aureus* Using Gold Nanostars

Materials and Methods

*Staphylococcus aureus* (ATCC 6538) was purchased from Cedarlane Labs (Oakville, Canada). Trypticase Soy Agar (TSA) plates, trypticase soy borth and Puritan® Calgiswab® were purchased from VWR International. Sodium chloride was purchased from Fisher Scientific. A 2.55% sodium chloride salt solution was prepared and sterilized by filtration. Then, 15 µL of trypticase soy broth was added to 250 mL of sterile saline to enhance the lifespan of bacteria.

*S. aureus* was cultured on a TSA plate by swabbing from stock plate in a sterile environment. The plate was then incubated at room temperature for two nights to allow for growth. A cloudy layer of bacteria was formed which indicated growth of live bacteria. 5 mL of saline was added to this plate and a swab was used to extract the bacteria from the plate to the solution. This solution was transferred to a 15 mL centrifuge tube and centrifuged at 4000 rpm for 10 minutes. The supernatant was discarded and the bacteria were resuspended in 5 mL saline solution. This gives the stock solution of *S. aureus* ($4.5 \times 10^8$ CFU/mL) and a diluted solution is obtained by adding 100 µL of stock solution to 9.9 mL of saline. Other serial dilutions were prepared and cultured for counting the colony forming units (CFU).

Figure 5:
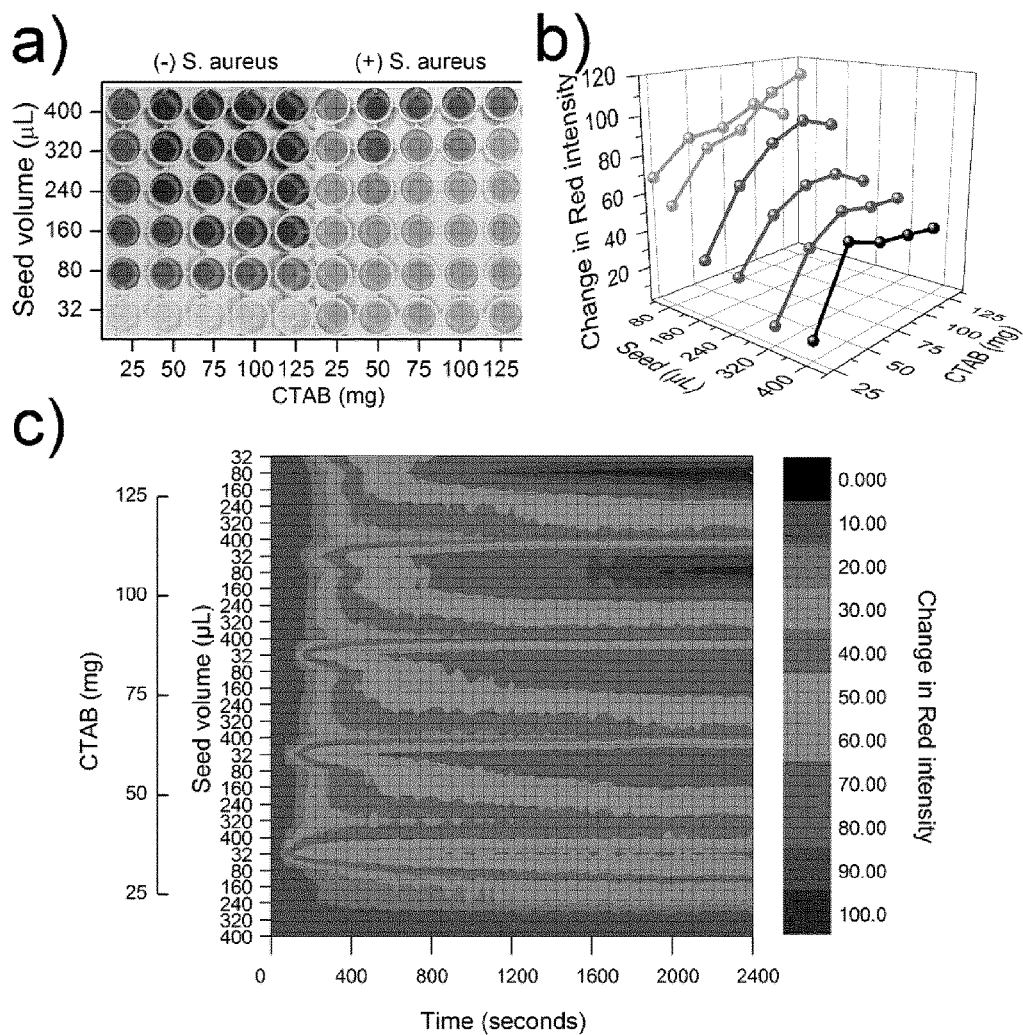
FIG. 5. Color change of gold nanostars in the presence of *Staphylococcus aureus*: a) Significant visible color change in the presence of $5 \times 10^5$ CFU/well *S. aureus* in a 96-well microplate; b) the final, maximum color change in the red component of RGB color model plotted against the gold seed and CTAB amounts; c) Evolution of the change in intensity of red component of color over time for each sample.

To perform the detection assay, 200 µL of gold nanostars with different colors, sizes and shapes were added to a 96-well microplate. Each of the gold nanostars solution was topped up with 100 µL of either saline, $4.5 \times 10^6$ CFU/mL *S. aureus*. A picture of the gold nanostars was taken after waiting for at least five minutes. These images are presented in FIG. 5. The images have been analyzed to determine their RGB values and change in RGB values compared to initial state. These results are plotted in FIG. 6.

Figure 7:
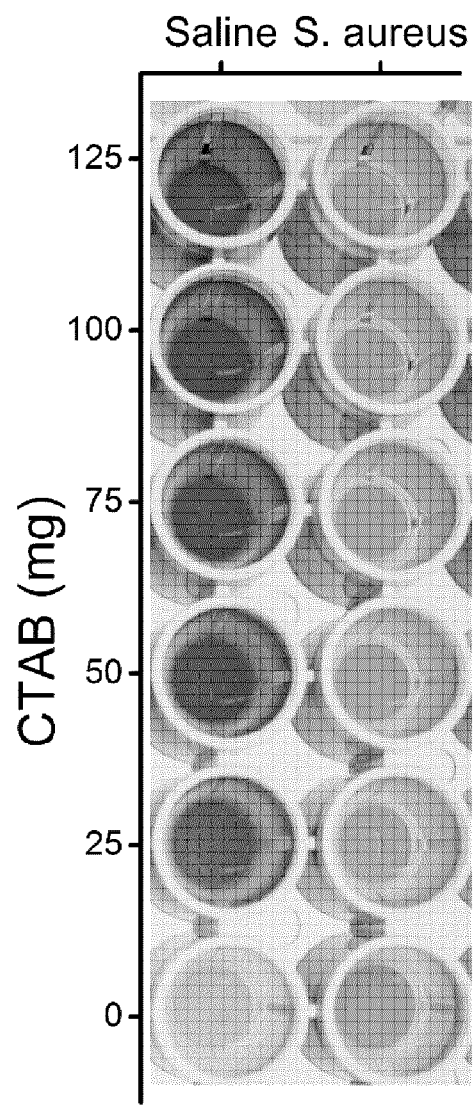
FIG. 7. Dependence on surfactant concentration. The effect of CTAB concentration on the ability to detect bacteria. Saline (2.25% with ~0.006% nutrient broth) was used as control and *S. aureus* was prepared at a baseline normalized absorption of 0.1 at 660 nm ($OD_{660}$).

The dependence of gold nanostar response on CTAB concentration was determined by centrifuging the gold nanostars at 10,000 rpm for 15 minutes and then resuspending in various concentrations of CTAB. The response was then compared and is demonstrated in FIG. 7.

Results and Discussion

Figure 6:
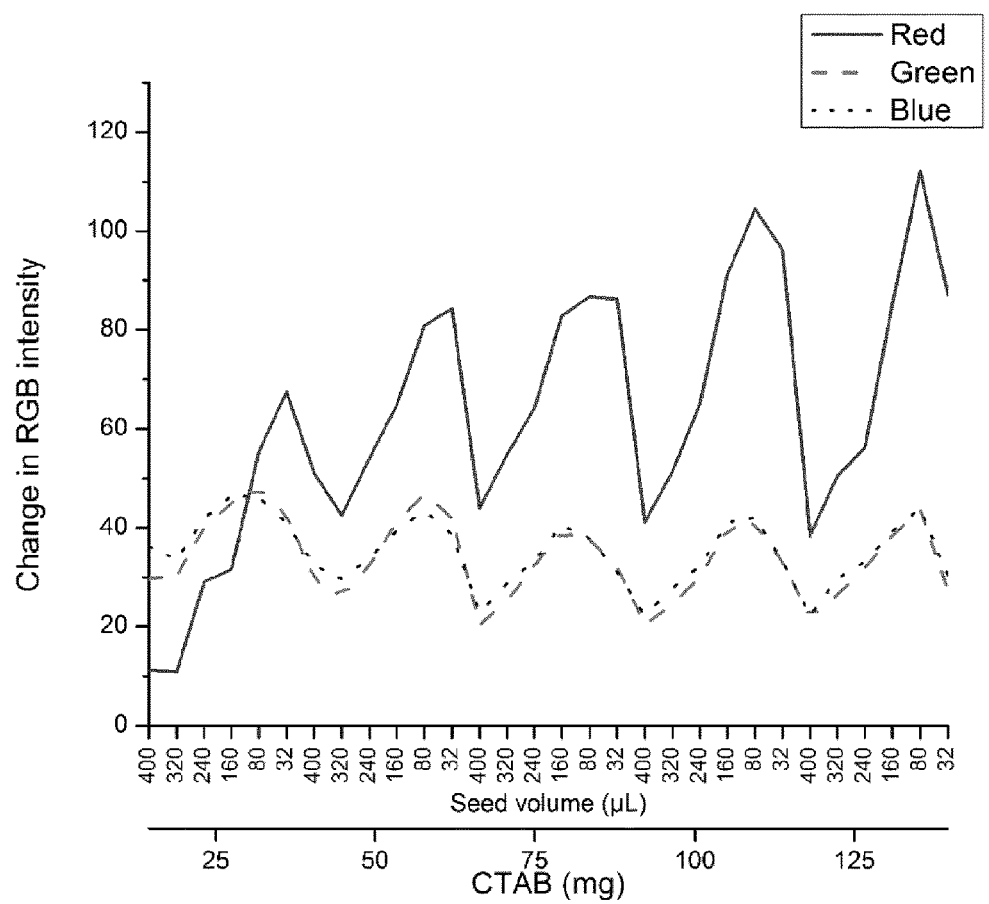
FIG. 6. Quantification of color change with bacteria. Maximum change in RGB values for color change in the presence of *S. aureus* is plotted against gold nanostar sample. The red component was found to have the greatest representation of color change for the nanostars. The blue and green components were found to correspond to the red components, as expected due to overall color change in the wells.

We tested the ability of each of the gold nanostars to detect the gram-positive bacteria S. aureus by adding them to gold nanostars in 96-well microplates. S. aureus was suspended in 2.55% saline solution (with ~0.006% broth) and thus this saline was used as a negative control. FIG. 5a) shows that the stars synthesized with the lowest seed amounts turn clear in saline (with ~0.006% broth) solution. This color change can be explained by the colloidal instability of larger gold nanostars. In contrast, smaller nanostars synthesized with higher seed values are more stable and only change color in the presence of S. aureus. While qualitative color change is intense and can be easily observed using the naked eye, quantification of the color was achieved by measuring the red, green and blue (RGB) components of each sample. We collected several images over two hours at an interval of about 25 seconds while leaving the samples undisturbed and then normalized each image with S. aureus by subtracting the initial image of gold nanostars. We measured the RGB values from each well and determined the maximum change in each component. The red component of RGB model showed the maximum change in intensity. Thus, the red component was plotted against the CTAB and gold seed amounts (FIG. 5b). This observation correlates closely with the light absorption peak and FWHM measured previously (FIG. 4c, d). The green and blue components also change in a similar manner but the magnitude of change is smaller (FIG. 6). FIG. 5b) suggests that more branched and larger nanostars show a greater color change in the presence of S. aureus. Interestingly, the general trend shown in FIG. 5b) matched the trend throughout our findings in both absorbance peak and FWHM, suggesting a consistent theme that the size and degree of branching of nanostars significantly impact optical properties and govern detection performance in a similar manner. We also studied the evolution of color change over time for each of the nanostars. Initial onset of color change was immediate and visually discernible in less than 5 minutes for most samples. This is seen in FIG. 5c) as the contour plot shows a change of up to 60 units of intensity within 300 seconds in the red component for the most sensitive gold nanostars. We observed that the color changes saturated after about 40 minutes. The plot confirms that the highest seed volume nanostars with smallest sizes and least branching show negligible color change due to high colloidal stability, while the most rapid color change occurs in nanostars synthesized using lowest seed volumes with biggest sizes and highest branching. This is in part because branching increases effective surface area and spatial extent, allowing gold nanostars to aggregate around the bacteria and therefore produce a more substantial change in color. The ideal formulation of nanostars will be stable in saline and change drastically in the presence of S. aureus. We quantified this criterion by subtracting the two images in FIG. 5a) and determining the RGB values of the subtracted image. Since the well red component demonstrates maximum change, the well with the highest difference in red provides the best formulation for application in pathogen detection. We observed that the nanostar solution synthesized using 125 mg CTAB and 240 µL gold nanoseed precursor was the optimal formulation. These nanostars have a small enough size to be stable in high salt concentrations and yet are branched enough to aggregate around S. aureus and cause a drastic color change. This optimal formulation of gold nanostars was used to test the effect of excess CTAB concentration on the detection of S. aureus. The results, seen in FIG. 7, demonstrate that there was negligible change between different concentrations of excess CTAB used. If the solution was devoid of CTAB (as in the Millipore water resuspension) after synthesis, gold nanostars would aggregate and change color in saline control as well. Thus, a small amount of CTAB is indeed necessary in solution after synthesis to prevent aggregation of the gold nanostars in saline (with ~0.006% broth).

Example 3: Comparison of Bacterial Response to Other Particles

In order to demonstrate selectivity, a solution of S. aureus was prepared in saline (with ~0.006% broth) to obtain normalized absorbance of 0.1 at 660 nm and this results in a concentration of approximately $8 \times 10^6$ CFU/well as determined by plate counts method. Since bacteria and particles cannot be exactly at the same concentration, they were compared by preparing the solutions at the same normalized absorbance of 0.1 at 660 nm. Polystyrene particles were diluted in saline (with ~0.006% broth). Liposomes were prepared according to manufacturer's recommendation. DMPC was dissolved in chloroform at a concentration of 10 mg/mL, while DMPG and DMPE were dissolved in a mixture of chloroform:methanol:water (65:35:8 v/v/v) at a concentration of 10 mg/mL. The phospholipid solutions were first dried under nitrogen and then in vacuo overnight. Saline (with ~0.006% broth) was added to the vials containing DMPC and DMPG at 30° C., and DMPE at 60° C. The phospholipids were allowed to rehydrate for several hours at the respective elevated temperatures. Size reduction was performed by sonicating each of the samples using a Branson probe sonicator for 10 minutes at 25% amplitude and 1 second on, 0.5 second off pulses. Each of the solutions were diluted in saline (with ~0.006% broth) to obtain the appropriate absorption. 100 µL of the particle solutions were then added to the 200 µL of optimal gold nanostar solution in a 96-well microplate. The solutions were incubated overnight and UV-Vis absorption spectra were obtained. These spectra are presented in FIG. 8.

Results and Discussion

Figure 8:
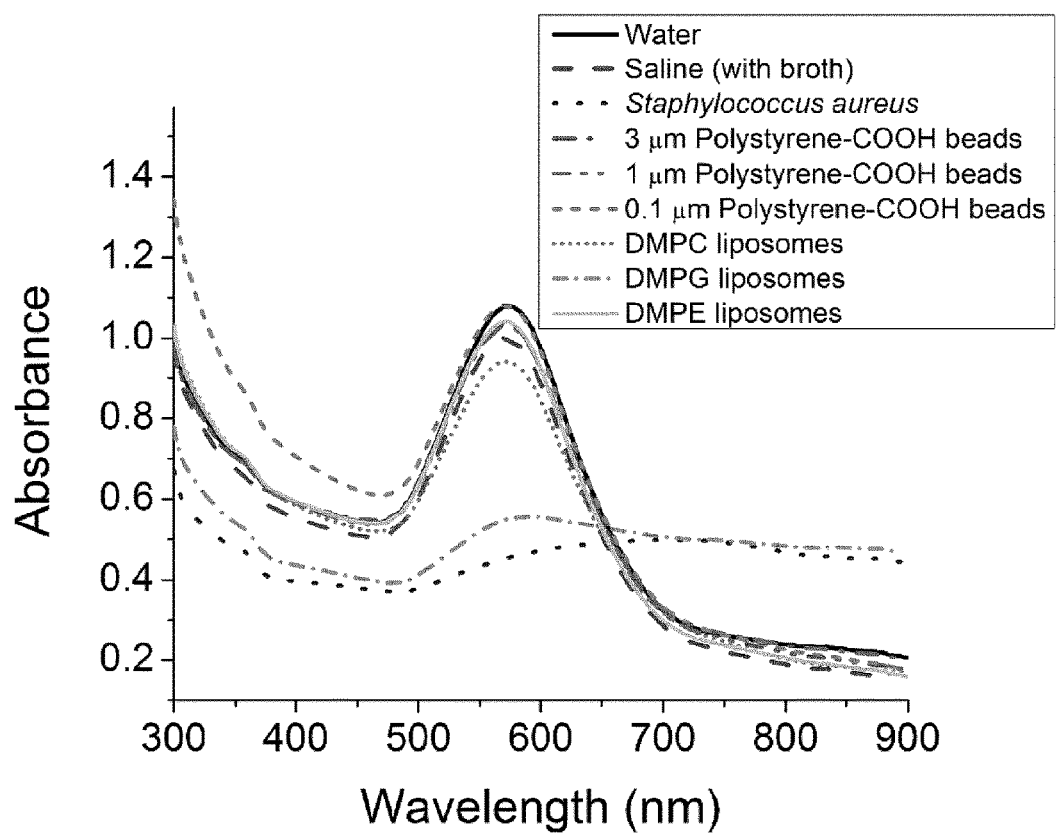
FIG. 8. Selectivity of an optimized formulation of gold nanostars. UV-UV-Visible absorption spectra of gold nanostars in water, in saline with broth, in the presence of *S. aureus*, in the presence of 3 μm, 1 μm and 0.1 μm carboxylic acid functionalized polystyrene particles, in the presence of 1,2-dimyristoyl-sn-glycero-3-phosphocholine (DMPC) liposomes, 1,2-dimyristoyl-sn-glycero-3-phospho-(1'-rac-glycerol) (DMPG) liposomes and 1,2-dimyristoyl-sn-glycero-3-phosphoethanolamine (DMPE) liposomes.

In order to better understand the cause of aggregation of CTAB-coated gold nanostars around S. aureus, we tested the interaction of gold nanostars with a variety of charged particles. Polystyrene microparticles functionalized with carboxylic acid were used to provide a negative surface charge, which has the potential to aggregate the positively charged CTAB-coated gold nanostars. Three different sizes of polystyrene microparticles were used to explore the effect of size on the aggregation of gold nanostars, where the 1 µm microparticles are most similar in size to S. aureus. We also used three different kinds of liposomes to explore the interaction between gold nanostars and charged phospholipids which could be responsible for the attraction between bacteria and gold nanostars. DMPC and DMPE terminate in a choline and ethanolamine group respectively and thus are zwitterionic. DMPG terminates in a glycerol group and hence the phosphate causes the liposomes to be overall negatively charged. FIG. 8 a) shows the UV-Vis spectra of the optimal formulation of gold nanostars (125 mg CTAB, 240 µL gold seed) in the presence of water, saline, *S. aureus*, polystyrene microparticles and phospholipids. The spectra in FIG. 8*a*) demonstrate minimal change in saline, polystyrene microparticles and DMPC and DMPE liposomes, while highlighting a drastic broadening and flattening of the peak in *S. aureus* and DMPG liposome solutions which confirms the shift in plasmon resonance of the gold nanostars. These spectra are consistent with the observed color change in the microplates from solid blue to a translucent grey in the presence of *S. aureus*. We confirmed that the color change of gold nanostars was due to near complete aggregation around the *S. aureus* (FIG. 13*a*) by imaging the samples using TEM. This aggregation is caused by electrostatic interactions between the CTAB-coated gold nanoparticle surface that is positively charged (zeta potential of +38.0 mV) and the cell wall of *S. aureus* that is negatively charged (zeta potential of −24.2 mV). Our results are in agreement with the work of Berry et al. (Berry et al., 2005) where they explained that the mechanism of aggregation of CTAB-coated gold nanorods around gram-positive *Bacillus cereus* is the strong electrostatic interactions between positively charged CTAB molecules and negatively charged teichoic acids on the surface of bacteria. Teichoic acid is expressed on the surface of gram-positive bacteria and it includes several phosphate groups, which provide a polyanionic surface with a high density of negative surface charge. As demonstrated by FIG. 8, a polyanionic surface is necessary for the aggregation of CTAB-coated gold nanostars since only negatively charged DMPG liposomes led to substantial aggregation. On the other hand, polystyrene particles with monoanionic carboxylic acid and zwitterionic liposomes had insufficient negative charge to cause a significant color change. Since only DMPG liposomes cause a color change comparable to bacteria, the aggregation of gold nanostars requires interaction with several negatively charged groups. Thus, the aggregation and color change of CTAB-coated gold nanostars is selective to bacteria and polyanionic particles in comparison to other particles with only monoanionic or zwitterionic charges. This work avoids the use of antibodies and aptamers and only exploits electrostatic interactions for colorimetric detection. Thus, there are some limits to specificity but since the distribution of charges is expected to be different in different strains of bacteria, these interactions can potentially be exploited developing a "chemical nose."

Example 4: Identification of Bacterial Strains Using Gold Nanoparticles

Materials and Methods

*S. aureus*, *Achromobacter xylosoxidans* (ATCC 27061), *Delftia acidovorans* (ATCC 15668) and *Stenotrophomonas maltophilia* (ATCC 13637) were purchased from Cedarlane Labs (Oakville, Canada) and inoculated on TSA plates and incubated at 37° C. for 24 hours. Bacterial cells were harvested using alginate swabs and suspended in 5 mL of sterile saline (2.55%) with nutrient broth (0.006%) in a 15 mL centrifuge tube. Each bacterial strain was then washed seven times with 2.55% saline (with ~0.006% nutrient broth) by centrifugation at 4,000 rpm for 10 min. The bacteria were then diluted to obtain an optical density at 660 nm ($OD_{660}$) of 0.1 (~$10^8$ CFU/mL (Dantam et al, 2011). When normalized against blank saline absorbance (0.033), this value becomes 0.067. When added to gold nanostars, the solution is diluted 1:3 to obtain final $OD_{660}$=0.02 for bacteria.

The assay for identification of bacterial strains was performed in 96-well microplates. The plates were prepared by adding 200 µL of blue, red or purple gold nanostars to the microplate wells. The training set was obtained by adding 100 µL of each bacteria (4 species) to the gold nanostars at final $OD_{660}$=0.02. Saline (with ~0.006% broth) was used as a control group. Each training group had 7-8 replicates. In order to obtain unknown samples, 14-18 samples from each group were selected and added randomly to a sterile storage microplate, resulting in a total of 79 samples. Each of these samples was then added to blue, red and purple gold nanostar solutions and incubated at room temperature overnight along with the training set.

After incubation, the microplates were illuminated by an X-ray film viewer and imaged using a Canon EOS Rebel T3 digital camera. For spectrophotometric identification, the UV-Visible absorption spectra were obtained for each well in the microplates using a BioTek Epoch microplate spectrophotometer while scanning from 300 nm to 900 nm with a step size of 1 nm, which have been presented in FIG. 11. The normalized absorbance values (presented in FIG. 12*a*) were obtained for all samples by using the following equation:

Normalized absorbance=(Average saline control absorbance at λ−Average saline control absorbance at 600 nm)−(Sample absorbance at λ−Sample absorbance at 600 nm)

where λ is the wavelength of particular importance: 583 nm peak for blue nanostars, 541 nm peak for red nanostars and 544 nm peak and 583 nm for purple nanostars. The absorbance at 800 nm was used as the baseline. The data was then subjected to a classical linear discriminant analysis (LDA) using MySTAT (version 12.02) and the canonical scores plot has been presented in FIG. 12*b*). Classification of unknown samples was performed by determining the shortest Mahalanobis distance to the groups generated using the training matrix. For the experiment of the identification of unknown bacteria samples, the experiment preparation and data collection were performed by two different researchers resulting in a blinded process.

Results and Discussion

Figure 9:
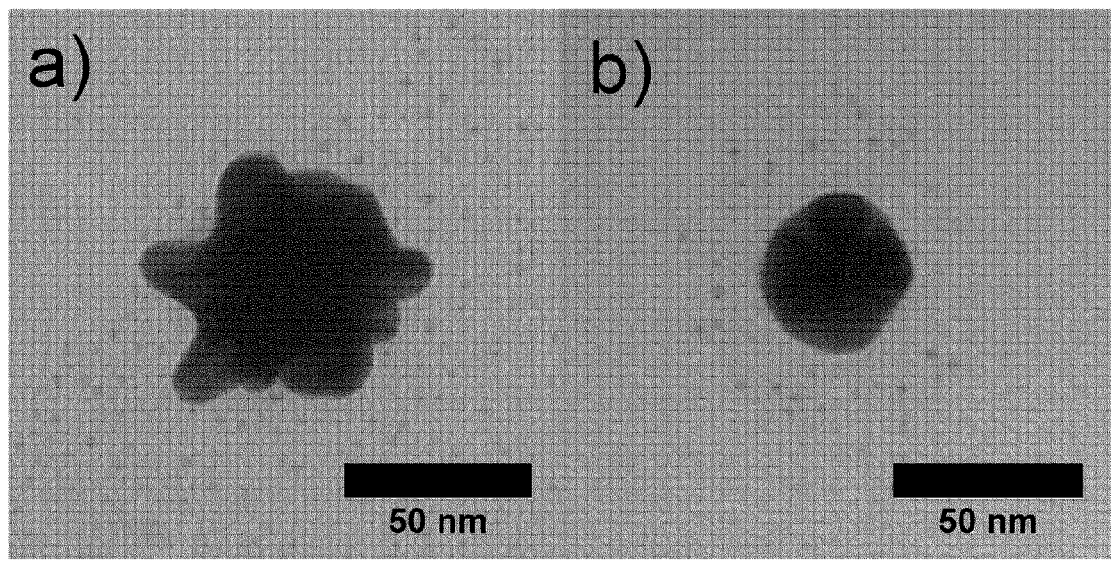
FIG. 9. TEM images of gold nanostars selected for "chemical nose". a) Gold nanostar with several branches referred to as 'blue' solution and b) Gold nanoparticles with almost no branches and referred to as 'red'.
Figure 10:
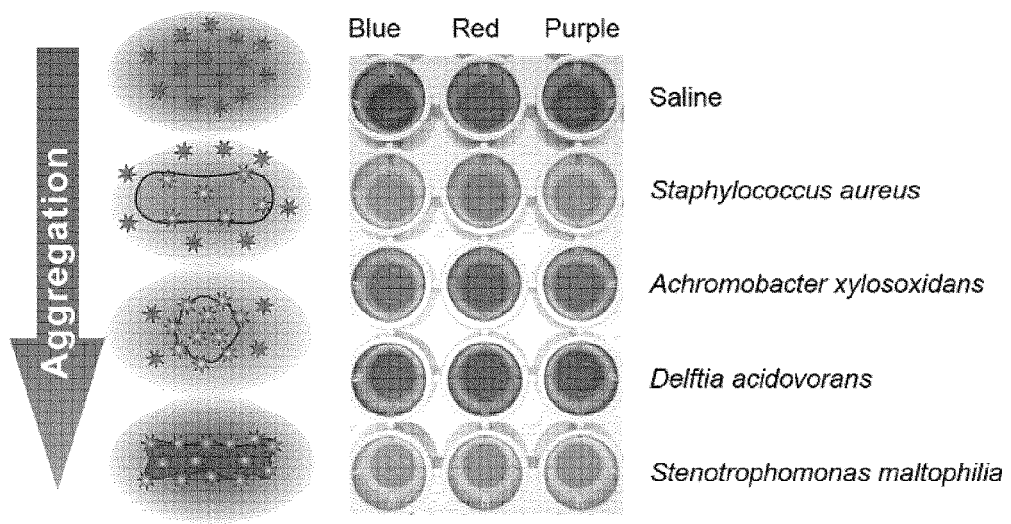
FIG. 10. Overview of bacteria identification. Change in color of gold nanostars caused by varying degrees of aggregation due to the differences in surface charge, surface area and morphology of bacteria. The photograph shows the color when different species of bacteria with final $OD_{660}$=0.02 are added to different gold nanostars.

In order to develop a "chemical nose," we need various gold nanoparticles that can interact with bacteria to provide a specific response. We hypothesize that if gold nanostars with different sizes and degrees of branching are incubated with a particular strain of bacteria, each nanostar will provide a unique colorimetric response. To test this hypothesis, we chose the commonly occurring Gram-positive *S. aureus* and Gram-negative ocular pathogens *A. xylosoxidans*, *D. acidovorans* and *S. maltophilia* as the pathogens of interest (Kilvington et al., 2013) and added them to gold nanostars to obtain a drastic colorimetric response. Two types of nanostars were synthesized such that there would be distinct differences in color (blue and red), size and degree of branching. Thus, each nanostar solution should interact differently between strains of bacteria depending on a strain's surface charge, surface area and morphology to provide a "chemical nose" sensor. The blue nanostars have a greater size and higher degree of branching as compared to the red nanostars, which are smaller and more spherical in shape (FIG. 9). These two nanostar solutions were also mixed 1:1 by volume to obtain a third solution of purple nanostars in order to investigate the co-operative response from the two nanoparticles. The three nanostar solutions were added to adjacent microplate wells and mixed with saline (as control) and different species of bacteria at the same optical density. A sample image is presented in FIG. 10, where the bacterial species are visually discernible. Amongst these species, *S. aureus* and *S. maltophilia* present the most striking differences as compared to saline. In the case of *S. aureus*, the gold nanostar solutions have a tinge of their respective original color whereas for *S. maltophilia*, the samples lose their original color and turn almost clear. This suggests a more complete aggregation of gold nanostars in the presence of *S. maltophilia* as compared to other species of bacteria. *D. acidovorans* and *A. xylosoxidans* produce a lower degree of color change. In the case of *D. acidovorans*, a color change of the red nanostars is seen to slightly purple, which is unique in comparison to other species. Thus, the red nanostars show a more drastic color change as compared to blue nanostars which allows for visual distinction between *A. xylosoxidans* and *D. acidovorans*. The purple nanostar solution behaves similar to blue stars in the case of *S. aureus* but it appears to be a superposition of blue and red nanostar responses in the presence of all other strains of bacteria.

Figure 11:
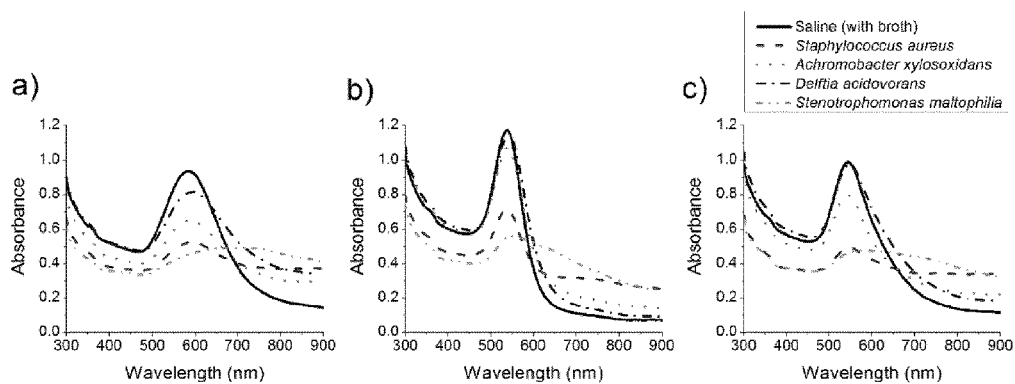
FIG. 11. Changes in absorption spectra of gold nanostars. Absorption spectra of gold nanostars upon addition of either saline (with broth) or bacteria with final $OD_{600}$=0.02: a) blue nanostars; b) red nanostars; c) purple nanostars.

The absorption spectra of each gold nanostar solution in the presence of bacteria are presented in FIG. 11. The observations from the spectra are consistent with the visual observations where *S. maltophilia* shows the most drastic change in spectra. In the case of blue nanostars, the peak with *S. maltophilia* is almost flattened whereas for red nanostars, there is partial flattening. The purple nanostar responses appear to be a linear combination of blue and red nanostars. In the case of *D. acidovorans*, while the absorbance peak does not drop significantly for red and purple nanostars, a red shift and drop is observed for blue nanostars (FIG. 11a). In all other bacterial species, the location of absorbance peak remains consistent but the absorbance values are reduced. Each gold nanostar solution has a unique absorption peak, which resembles the localized surface plasmon resonance wavelength. As shown in FIG. 11, blue and red nanostars have peaks at 583 nm and 541 nm respectively. Purple nanostars have a peak at 544 nm (close to that of red nanostars); however, the absorbance at 583 nm is also of interest to determine the response characteristics from the blue nanostars constituents. The absorbance at 541 nm of red nanostars constituents were not found to be important since it was close to the natural peak of 544 nm of purple nanostars. The absorbance values from these peaks were obtained and normalized against saline with broth as well as baseline absorbance at 800 nm. These normalized values are presented in FIG. 12a) and demonstrate that each species of bacteria interacts in a unique manner with blue, red and purple nanostar solutions. We further analyzed these normalized values to create a training set for the identification of species of bacteria.

Using LDA, we observed that identification of each population of bacteria was possible by using the two normalized absorbance values from purple nanostars (544 nm and 583 nm). This is demonstrated in FIG. 12b), where each species of bacteria as well as saline control is statistically discernable using 95% confidence intervals. This training set was then used to identify unknown samples using MyStAT (p>0.95), and it was demonstrated that 99% (78/79 samples) of the samples could be identified accurately with their respective group. These are noteworthy results since only two inputs are being used to identify five different populations of samples. It has been demonstrated that the unique surface charge on different strains of bacteria can be utilized for identification when electrostatic interactions are used (Phillips et al., 2008). Previous work required the modification of gold nanoparticles with a variety of molecules to provide unique surface charges and hydrophobicity for enhancing the interaction with bacteria. Additionally, these gold nanoparticles are generally coupled with fluorescent polymers, which provide the response and hence require fluorescence spectrometry. In the present study, identifying bacterial strains was possible visually as well spectrophotometrically. We exploit the inherent properties of gold nanostars rather than modifying them with specific surface ligands. The CTAB surfactant of gold nanostars is present on as-synthesized nanoparticles and serves as the source of positive surface charge. We have shown previously that the CTAB-coated nanostars require a polyanionic surface for aggregation and color change change (Verma et al., 2014). Such a polyanionic surface is generally provided in Gram-positive bacteria by teichoic acids (Berry and Saraf, 2005; Berry et al., 2005) and in Gram-negative bacteria by lipopolysaccharides and phospholipids (Sun et al., 2012; Hong and Brown, 2006). The intrinsically different distribution of charges on the surface of bacteria is responsible for causing the unique electrostatic interactions with gold nanostars. It is expected that gold nanostars with significant protruding branches will interact more strongly with the surface of bacteria due to higher effective surface area and spatial extent as compared to more spherical nanostars (Verma et al., 2014). These inherent differences in branching and size provide different colorimetric outputs since their localized surface plasmon resonance is sensitive to the degree of aggregation (Xia et al., 2010).

Example 5: Transmission Electron Microscopy of Bacteria and Gold Nanostars

Materials and Methods

Blue gold nanostars were chosen as a representative sample for imaging using transmission electron microscopy (TEM). Samples were prepared by adding 5 µL of the overnight incubated bacteria and gold nanostars solution to copper TEM grids and allowed to dry under ambient conditions overnight. Once dry, the sample was washed by placing 5 µL of Millipore water on the TEM grid for 30 seconds and then wicking the liquid using filter paper to remove excess surfactants, salts and unbound gold nanostars. The samples were then imaged using Phillips CM10 TEM. The total number of gold nanostars aggregated around the surface of each bacterium was manually counted using the National Institutes of Health ImageJ software (n=8). These numbers have been presented in FIG. 12a) and the TEM images have been shown in FIG. 13.

Results and Discussion

Figure 12:
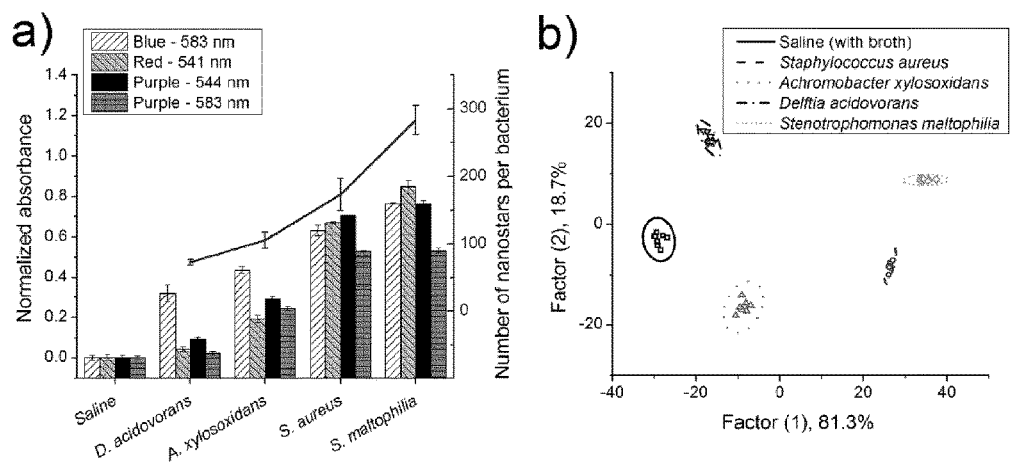
FIG. 12. Analysis of peaks from absorption spectra. Response of gold nanostars to saline (with broth) control and different species of bacteria with final $OD_{660}$=0.02: a) Normalized absorbance response (n=7-8; mean±S.D.) and average number of aggregated gold nanostars per bacterium by TEM (n=8; mean±S.E.). b) Canonical scores plot of the response from Linear Discriminant Analysis (LDA) of purple nanostars (544 nm and 583 nm) for different species of bacteria. 95% confidence ellipses are presented for each population.
Figure 13:
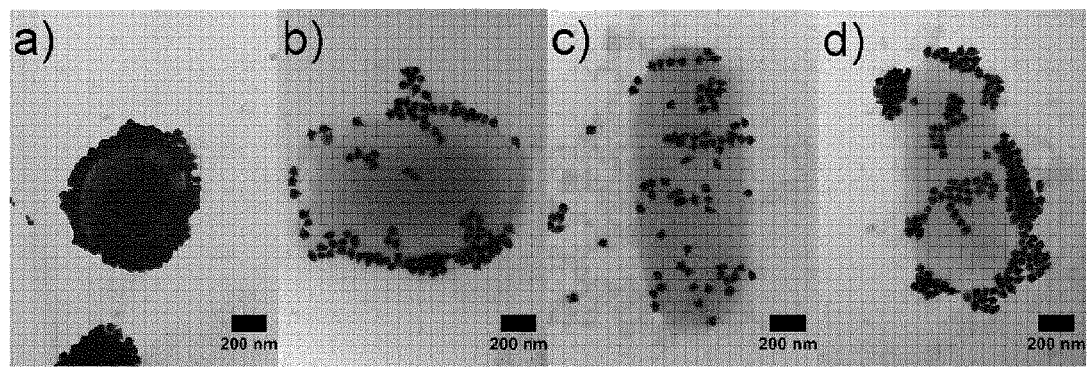
FIG. 13. TEM images of gold nanostars aggregating around bacteria. a) *Staphylococcus aureus*, b) *Achromobacter xylosoxidans*, c) *Delftia acidovorans*, d) *Stenotrophomonas maltophilia*. Scale bars are 200 nm each.

We used TEM to confirm that the gold nanostars are aggregating around the bacteria of interest (FIG. 13). It is observed that gold nanostars aggregate around bacteria with different shapes (spherical or rod-like) as well as types (Gram-positive or Gram-negative). The TEM samples were rinsed with Millipore water once before drying to remove excess gold nanostars and assist in visualization. Since gold nanostars remained on the bacteria even after rinsing, the images suggest a strong electrostatic interaction, which governs the degree of aggregation and hence the colorimetric response provided by the gold nanostars. This is shown in FIG. 12a) since a close correlation is observed between the number of gold nanostars aggregating per bacterium and the normalized absorbance observed for the blue nanostars. In contrast to the results reported in FIG. 12a), at the relevant pH (~7) and electrolytic condition (0.85% NaCl, 1:1) one might expect that *S. aureus* would have a greater number of gold nanostars aggregated—thus greater normalized absorbance—when compared to *S. maltophilia* due to surface charge since the former is Gram-positive and the latter is Gram-negative (Hong and Brown, 2008). Moreover, there appears to be a higher density of gold nanostars aggregated around *S. aureus* than *S. maltophilia* in FIGS. 13a) and 13d), respectively. However, total gold nanostar aggregation response depends on surface area in addition to surface charge as previously mentioned. Thus, as seen in the TEM images the greater size and rod shape of *S. maltophilia* leads to a much greater surface area. In spite of *S. aureus* being Gram-positive, the combination of greater surface area and relatively high number of polyanionic surface charges of *S. maltophilia* yield to a greater number of total gold nanostar aggregated per bacterium and thus a greater normalized response, as was reported.

In addition to the number of gold nanostars per bacterium, the pattern of aggregation also seems to be unique. For example, in FIG. 13c), the gold nanostars around *D. acidovorans* are distributed throughout the cell and form a sparse coating. On the other hand, in FIG. 13d), there appear to be patches of aggregated gold nanostars in localized areas on the surface of *S. maltophilia*, while some areas are completely devoid of gold nanostars. In a previous study, the aggregation of 6 nm cationic gold nanoparticles has shown a unique aggregation pattern around the gram-positive bacteria *Bacillus subtilis* as compared to the gram-negative *Escherichia coli* (Hayden et al., 2012). It was demonstrated that the patterns disappeared in the once the bacteria were exposed to proteolytic cleavage suggesting the importance of surface proteins in the aggregation of gold nanoparticles (Scott and Barnett, 2006). We demonstrate that aggregation patterns are not limited to gram-positive bacteria as they also appeared on gram-negative *S. maltophilia* (FIG. 13d). Gold nanostars can be thus used as probes for exploring the surface morphology, protein and lipid distribution, and local charge densities of bacteria in future studies.

Additionally, aggregation of gold nanoparticles around bacteria has been observed when they were modified with specific antibodies against the bacteria (Khan et al., 2011; Ho et al., 2004) but these studies typically detect a single bacterial species. In past work, biomodification becomes necessary when the detection of multiple species or strains of bacteria is involved (Wang et al, 2008); however, in the current work we have demonstrated the ability to distinguish between species without adding specific ligands to the surface of gold nanostars, while relying on the intrinsic response of gold nanostars to bacteria instead.

Example 6: Quantification of Various Species of Bacteria

Materials and Methods

Figure 14:
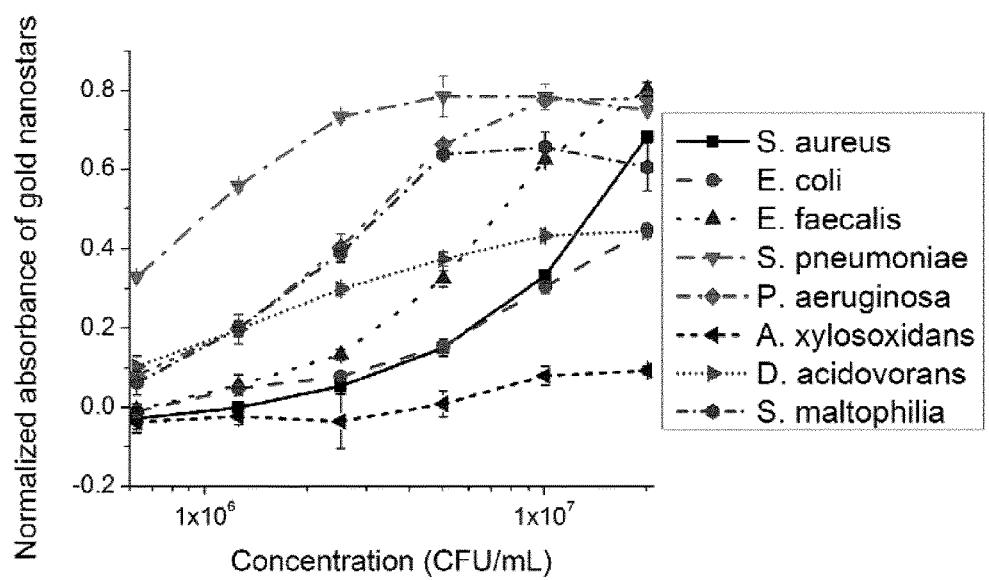
FIG. 14. Concentration dependent response of bacteria. Normalized absorbance response for purple gold nanostars in the presence of *S. aureus, E. coli, E. faecalis, S. pneumoniae, P. aeruginosa, A. xylosoxidans, D. acidovorans* and *S. maltophilia* at different concentrations.
Figure 15:
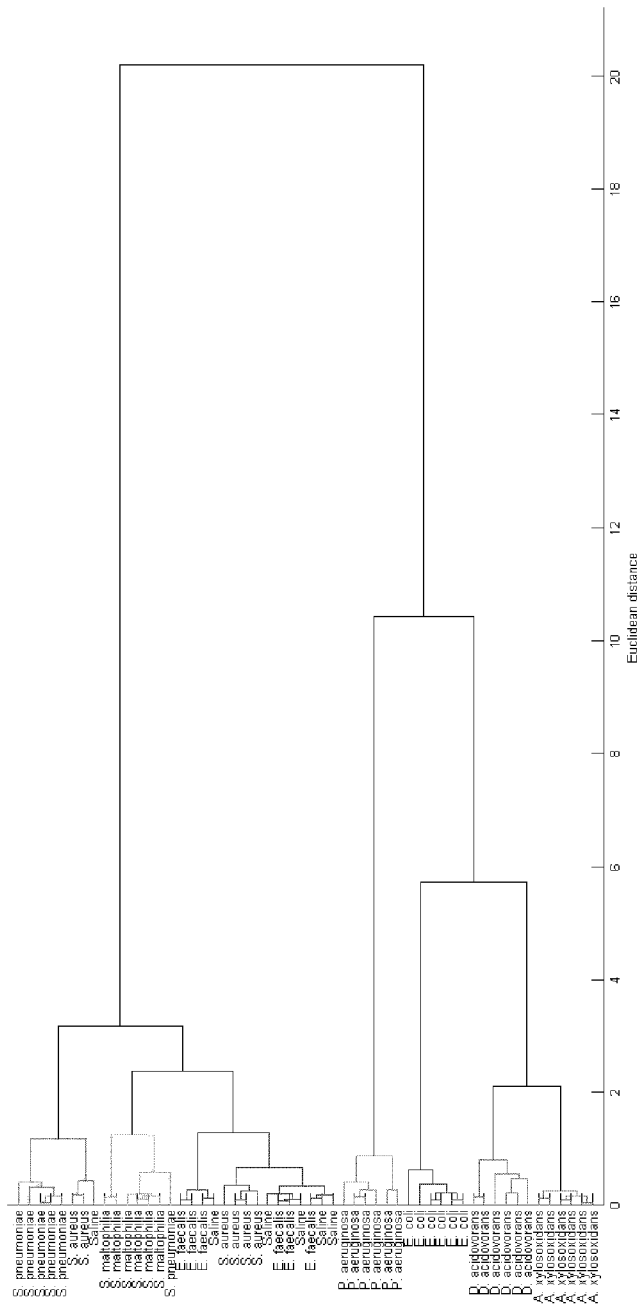
FIG. 15. Dendrogram representing hierarchical clustering analysis. Most populations of species and strains of bacteria can be distinguished because of their unique responses.

Additional species of bacteria: *Escherichia coli* (ATCC 10798), *Streptococcus pneumoniae* (ATCC 6305), *Enterococcus faecalis* (ATCC 29212) and *Pseudomonas aeruginosa* (ATCC 9027) were purchased from Cedarlane Labs (Oakville, Canada). *E. coli* and *P. aeruginosa* were cultured in TSA plates at 37° C. overnight while *E. faecalis* and *S. pneumoniae* were cultured on Blood agar plates at 37° C. *S. pneumonia* was incubated in a $CO_2$ incubator with 5% $CO_2$. These bacteria were then extracted and washed as explained in Example 6. The bacteria were then normalized to $OD_{660}=1.0$ ($1\times10^9$ CFU/mL) and serially diluted by a factor of 2 to obtain 16×-512× dilution. Each of these dilutions of bacteria was added to purple gold nanostars and the absorbance was measured after overnight incubation. The peak absorbance was normalized and plotted against the approximate concentration in FIG. 14. One concentration (128× dilution) was selected for performing hierarchical clustering analysis and the resulting dendrogram is presented in FIG. 15.

Results and Discussion

We wanted to examine whether the response from gold nanostars could be used for quantification and identification of a larger library of pathogens. We added the following organisms to our tests: *Escherichia coli*, *Pseudomonas aeruginosa*, *Streptococcus pneumoniae* and *Enterococcus faecalis*. These organisms were normalized to the same $OD_{600}=1.0$ and then serially diluted to obtain several concentrations. The concentration dependent response presented in FIG. 14 suggests that each bacterium provides a unique curve, which can be used for its quantification. Additionally, a single concentration was chosen to perform hierarchical clustering analysis. The resulting dendrogram is presented in FIG. 15 and it demonstrates that most of the bacteria had their own population and were not separated by large distances. There were some outliers in the data which led to confusion of the grouping but overall, the dendrogram suggests that it is possible to identify and quantify the bacterial species or strain present using a spectrometer with reasonable accuracy. The simplicity and rapid response of the assay gives the potential of implementation in a consumer product.

The above-described embodiments are intended to be examples only. Alterations, modifications and variations can be effected to the particular embodiments by those of skill in the art without departing from the scope of the disclosure, which is defined solely by the claims appended hereto.

All references cited throughout the specification are incorporated by reference in their entirety.

LIST OF REFERENCES

Berry, V., Gole, A., Kundu, S., Murphy, C. J., Saraf, R. F., Deposition of CTAB-terminated nanorods on bacteria to form highly conducting hybrid systems. Journal of the American Chemical Society 2005, Volume 127, Issue 50, pp 17600-17601.

Berry, V., Saraf, R. F., Self-assembly of nanoparticles on live bacterium: an avenue to fabricate electronic devices. Angewandte Chemie (International ed. in English) 2005, Volume 44, Issue 41, pp 6668-6673.

Chen, H. M., Peng, H. C., Liu, R. S., Asakura, K., Lee, C. L., Lee, J. F., Hu, S. F., Controlling the length and shape of gold nanorods. The journal of physical chemistry. B 2005, Volume 109, Issue 42, pp 19553-19555.

Dantam, J., Zhu, H., Stapleton, F., Biocidal efficacy of silver-impregnated contact lens storage cases in vitro. Investigative ophthalmology & visual science 2011, Volume 52, Issue 1, pp 51-57.

Grzelczak, M., Perez-Juste, J., Mulvaney, P., Liz-Marzan, L. M., Shape control in gold nanoparticle synthesis. Chemical Society Reviews 2008, Volume 37, Issue 9, pp 1783-1791.

Hao, F., Nehl, C. L., Hafner, J. H., Nordlander, P., Plasmon resonances of a gold nanostar. Nano letters 2007, Volume 7, Issue 3, pp 729-732.

Hayden, S. C., Zhao, G., Saha, K., Phillips, R. L., Li, X., Miranda, O. R., Rotello, V. M., EI-Sayed, M. A., Schmidt-Krey, I., Bunz, U. H., Aggregation and interaction of cationic nanoparticles on bacterial surfaces. Journal of the American Chemical Society 2012, Volume 134, Issue 16, pp 6920-6923.

He Sha, Liu DingBin, Wang Zhuo, Cai KaiYong, Jiang XingYu, Utilization of unmodified gold nanoparticles in calorimetric detection. Science China-Physics Mechanics & Astronomy 2011, Volume 54, Issue 10, pp 1757-1765.

Ho, K. C., Tsai, P. J., Lin, Y. S., Chen, Y. C., Using biofunctionalized nanoparticles to probe pathogenic bacteria. Analytical Chemistry 2004, Volume 76, Issue 24, pp 7162-7168.

Hong, Y., Brown, D. G., Electrostatic behavior of the charge-regulated bacterial cell surface. Langmuir: the ACS journal of surfaces and colloids 2008, Volume 24, Issue 9, pp 5003-5009.

Hong, Y., Brown, D. G., Cell surface acid-base properties of *Escherichia coli* and *Bacillus brevis* and variation as a function of growth phase, nitrogen source and C:N ratio. Colloids and surfaces. B, Biointerfaces 2006, Volume 50, Issue 2, pp 112-119.

Khan, S. A., Singh, A. K., Senapati, D., Fan, Z., Ray, P. C., Targeted highly sensitive detection of multi-drug resistant *Salmonella* DT104 using gold nanoparticles. Chemical communications (Cambridge, England) 2011, Volume 47, Issue 33, pp 9444-9446.

Kilvington, S., Shovlin, J., Nikolic, M., Identification and susceptibility to multipurpose disinfectant solutions of bacteria isolated from contact lens storage cases of patients with corneal infiltrative events. Contact lens & anterior eye: the journal of the British Contact Lens Association 2013, Volume 36, Issue 6, pp 294-298.

Link, S., EI-Sayed, M. A., Shape and size dependence of radiative, non-radiative and photothermal properties of gold nanocrystals. International Reviews in Physical Chemistry 2000, Volume 19, Issue 3, pp 409-453.

Lu, W., Singh, A. K., Khan, S. A., Senapati, D., Yu, H., Ray, P. C., Gold nano-popcorn-based targeted diagnosis, nanotherapy treatment, and in situ monitoring of photothermal therapy response of prostate cancer cells using surface-enhanced Raman spectroscopy. Journal of the American Chemical Society 2010, Volume 132, Issue 51, pp 18103-18114.

Min-Chen, Hao, Liu, Ru-Shi, Tsai, Din Ping, A Versatile Route to the Controlled Synthesis of Gold Nanostructures. Crystal Growth & Design 2009, Volume 9, Issue 5, pp 2079-2087.

Nehl, C. L., Liao, H., Hafner, J. H., Optical properties of star-shaped gold nanoparticles. Nano letters 2006, Volume 6, Issue 4, pp 683-688.

Phillips, R. L., Miranda, O. R., You, C. C., Rotello, V. M., Bunz, U. H., Rapid and efficient identification of bacteria using gold-nanoparticle-poly(para-phenyleneethynylene) constructs. Angewandte Chemie (International ed. in English) 2008, Volume 47, Issue 14, pp 2590-2594.

Sau, T. K., Rogach, A. L., Nonspherical noble metal nanoparticles: colloid-chemical synthesis and morphology control. Advanced materials (Deerfield Beach, Fla.) 2010, Volume 22, Issue 16, pp 1781-1804.

Scott, J. R., Barnett, T. C., Surface proteins of gram-positive bacteria and how they get there. Annual Review of Microbiology 2006, Volume 60, pp 397-423.

Sun, Jiayu, Ge, Jiechao, Liu, Weimin, Wang, Xueliang, Fan, Zhiyuan, Zhao, Wenwen, Zhang, Hongyan, Wang, Pengfei, Lee, Shuit-Tong, A facile assay for direct colorimetric visualization of lipopolysaccharides at low nanomolar level. Nano Research 2012, Volume 5, Issue 7, pp 486-493.

Sun, Y., Xia, Y., Shape-controlled synthesis of gold and silver nanoparticles. Science (New York, N.Y.) 2002, Volume 298, Issue 5601, pp 2176-2179.

Verma, Mohit S., Chen, Paul Z., Jones, Lyndon, Gu, Frank X., Branching and size of CTAB-coated gold nanostars control the colorimetric detection of bacteria. RSC Advances 2014, Volume 4, Issue 21, pp 10660-10668.

Wang, C., Irudayaraj, J., Gold nanorod probes for the detection of multiple pathogens. Small (Weinheim an der Bergstrasse, Germany) 2008, Volume 4, Issue 12, pp 2204-2208.

Wu, Hsin-Lun, Chen, Chiu-Hua, Huang, Michael H., Seed-Mediated Synthesis of Branched Gold Nanocrystals Derived from the Side Growth of Pentagonal Bipyramids and the Formation of Gold Nanostars. Chemistry of Materials 2009, Volume 21, Issue 1, pp 110-114.

Xia, F., Zuo, X., Yang, R., Xiao, Y., Kang, D., Vallee-Belisle, A., Gong, X., Yuen, J. D., Hsu, B. B., Heeger, A. J., Plaxco, K. W., Colorimetric detection of DNA, small molecules, proteins, and ions using unmodified gold nanoparticles and conjugated polyelectrolytes. Proceedings of the National Academy of Sciences of the United States of America 2010, Volume 107, Issue 24, pp 10837-10841.

Xiao, J., Qi, L., Surfactant-assisted, shape-controlled synthesis of gold nanocrystals. Nanoscale 2011, Volume 3, Issue 4, pp 1383-1396.

Yuan, H., Khoury, C. G., Hwang, H., Wilson, C. M., Grant, G. A., Vo-Dinh, T., Gold nanostars: surfactant-free synthesis, 3D modelling, and two-photon photoluminescence imaging. Nanotechnology 2012, Volume 23, Issue 7, pp 075102-4484/23/7/075102. Epub 2012 Jan. 20.

What is claimed is:

1. A method of directly detecting a pathogen in a sample comprising:
   a) obtaining a sample suspected of containing a pathogen;
   b) contacting the sample with a plurality of unmodified metallic nanoparticles under conditions suitable to permit direct association of the nanoparticles with a surface of the pathogen, if present,
   wherein the surface comprises teichoic acids, lipids, polysaccharides and/or proteins, and wherein the pathogen is not modified prior to the contacting; and
   c) assessing the direct association of the nanoparticles with the surface of the pathogen to determine whether the pathogen is present or absent,
   wherein assessing the association of the nanoparticles with the pathogen comprises assessing a colorimetric property of the sample.

2. The method of claim 1, wherein the colorimetric property is assessed visually or spectrophotometrically.

3. The method of claim 1, wherein the presence or absence of pathogen is determined by comparing the colorimetric property of the sample to a control.

4. The method of claim 1, wherein the metallic nanoparticles are gold nanoparticles.

5. The method of claim 4, wherein the nanoparticles are less than about 1000 nm, less than about 500 nm, less than about 400 nm, less than about 300 nm, less than about 200 nm, less than about 150 nm, less than 100 nm, less than 90 nm, less than about 80 nm, less than about 70 nm, less than about 60 nm, less than about 50 nm, less than about 40 nm, less than about 35 nm, less than about 30 nm, less than about 25 nm, less than about 20 nm, less than about 15 nm, less than about 10 nm, less than about 9 nm, less than about 8 nm, less than about 7 nm, less than about 6 nm, less than about 5 nm, less than about 4 nm, less than about 3 nm, less than about 2 nm, less than about 1 nm.

6. The method of claim 4, wherein the nanoparticles have branches.

7. The method of claim 1, wherein the nanoparticles comprise a mixture of two or more distinct populations of nanoparticles.

8. The method of claim 1, wherein the pathogen is bacteria.

9. The method of claim 1, wherein the sample is a non-biological sample.

10. The method of claim 1, further comprising identifying the pathogen.

11. The method of claim 10, wherein identifying comprises comparing the colorimetric property of the sample to one or more positive controls containing known pathogen.

12. The method of claim 11, wherein identifying comprises comparing the colorimetric property of the sample, or the pattern of nanoparticle association on the surface of the pathogen, to unique fingerprints for known pathogens.

13. The method of claim 1, for distinguishing between two or more different bacteria.

14. The method of claim 1, further comprising quantifying the pathogen.

15. A method of identifying a pathogen in a sample, comprising:
   a) contacting a sample suspected of containing a pathogen with a plurality of unmodified metallic nanoparticles under conditions suitable to permit direct association of the nanoparticles with a surface of the pathogen, wherein the surface comprises teichoic acids, lipids, polysaccharides and/or proteins, and wherein the pathogen is not modified prior to the contacting; and
   b) comparing a colorimetric property of the sample and/or the pattern of nanoparticle association on the surface of the pathogen to unique fingerprints for known pathogens.

16. The method of claim 15, wherein the nanoparticles comprise a mixture of two or more distinct populations of nanoparticles.

* * * * *